(12) United States Patent
Kim et al.

(10) Patent No.: US 11,583,497 B2
(45) Date of Patent: Feb. 21, 2023

(54) NANO-EMULSION OF CBFß-RUNX1 INHIBITOR FOR OCULAR DRUG DELIVERY

(71) Applicant: The Schepens Eye Research Institute, Inc., Boston, MA (US)

(72) Inventors: Leo A. Kim, Brookline, MA (US); Joseph F. Arboleda-Velasquez, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 16/763,932

(22) PCT Filed: Nov. 14, 2018

(86) PCT No.: PCT/US2018/061156
§ 371 (c)(1),
(2) Date: May 13, 2020

(87) PCT Pub. No.: WO2019/099595
PCT Pub. Date: May 23, 2019

(65) Prior Publication Data
US 2020/0375899 A1 Dec. 3, 2020

Related U.S. Application Data

(60) Provisional application No. 62/586,027, filed on Nov. 14, 2017.

(51) Int. Cl.
| | | |
|---|---|---|
| A61K 9/00 | (2006.01) | |
| A61K 9/107 | (2006.01) | |
| A61K 31/5513 | (2006.01) | |
| A61K 47/10 | (2017.01) | |
| A61K 47/14 | (2017.01) | |
| A61K 47/24 | (2006.01) | |
| A61K 9/19 | (2006.01) | |

(52) U.S. Cl.
CPC ........ *A61K 9/1075* (2013.01); *A61K 31/5513* (2013.01); *A61K 47/10* (2013.01); *A61K 47/14* (2013.01); *A61K 47/24* (2013.01); *A61K 9/0048* (2013.01); *A61K 9/19* (2013.01)

(58) Field of Classification Search
CPC ...... A61K 9/0048; A61K 9/1075; A61K 9/19; A61K 31/5513; A61K 47/10; A61K 47/14; A61K 47/24
See application file for complete search history.

(56) References Cited

U.S. PATENT DOCUMENTS

| | | | |
|---|---|---|---|
| 3,405,122 A | 10/1968 | Berger et al. | |
| 4,652,441 A | 3/1987 | Okada et al. | |
| 4,675,189 A | 6/1987 | Kent et al. | |
| 5,019,400 A | 5/1991 | Gombotz et al. | |
| 5,036,101 A | 7/1991 | Hsu et al. | |
| 5,041,438 A | 8/1991 | Hsu | |
| 5,141,735 A | 8/1992 | Bellemin et al. | |
| 5,164,376 A | 11/1992 | Hsu et al. | |
| 5,641,773 A | 6/1997 | Pardee et al. | |
| 6,630,477 B1 | 10/2003 | Daluge | |
| 6,709,650 B1 | 3/2004 | Sutton et al. | |
| 2012/0039978 A1* | 2/2012 | Moscona | A61P 31/12 424/490 |
| 2014/0004082 A1 | 1/2014 | Liu et al. | |
| 2014/0275263 A1 | 9/2014 | Wassel et al. | |
| 2016/0101050 A1* | 4/2016 | Lee | A61K 47/26 424/278.1 |
| 2016/0208246 A1 | 7/2016 | Groner et al. | |
| 2019/0350961 A1 | 11/2019 | Arboleda-Velasquez et al. | |
| 2020/0102384 A1 | 4/2020 | Arboleda-Velasquez et al. | |
| 2020/0103419 A1 | 4/2020 | Arboleda-Velasquez et al. | |
| 2020/0377888 A1 | 12/2020 | Kim et al. | |

OTHER PUBLICATIONS

Witvrouw et al. Antimicrobial Agents and Chemotherapy. 1992; 36(12): 2628-2633. (Year: 1992).*
Mishra et al., "Nanoemulsion: A Novel Drug Delivery Tool", Jul. 2014 (Jul. 2014), International Journal of Pharma Research & Review, Jul. 2014; 3(7):32-43; entire document especially abstract.
Wikipedia, "Lecithin". Nov. 1, 2017 (Nov. 1, 2017 ), retrieved on Feb. 27, 2019 from https://en.wikipedia.org/w/index.php?title=Lecithin&oldid=808162031; <http://en.wikipedia.org/w/index.php?title=Lecithin&oldid=808162031;> entire document, especially p. 1 para 4.
Head et al., "Ocular pathology of uncommon hematologic malignancies: a case series", Nov. 28, 2007 (Nov. 28, 2007), Journal of Medical Case Reports 2007, 1:158 doi:10.1186/1752-1947.1.158; entire document, especially abstract.
Written Opinion of the International Searching Authority for International Patent Application No. PCT/US2018/061156 dated Mar. 14, 2019 (5 pages).
International Search Report for International Patent Application No. PCT/US2018/061156 dated Mar. 14, 2019 (3 pages).
Cunningham et al., "Identification of benzodiazepine Ro5-3335 as an inhibitor of CBF leukemia through quantitative high throughput screen against RUNX1-CBFβ interaction," Proc Natl Acad Sci USA, 2012, 109(36):14592-14597.
Illendula et al., "Small Molecule Inhibitor of CBFβ-RUNX Binding for RUNX Transcription Factor Driven Cancers," EBioMedicine, 2016, 8:117-131.
PCT International Preliminary Report on Patentability in International Appln. No. PCT/US2018/061156, dated May 19, 2020, 6 pages.
Syed et al., "Novel Treatments for Corneal Angiogenesis," Int Ophthalmol Clin., 2017, 57(4):31-38.

(Continued)

*Primary Examiner* — David Browe
(74) *Attorney, Agent, or Firm* — Fish & Richardson P.C.

(57) ABSTRACT

The invention provides ocular formulations and features a nano-emulsion composition, e.g., a nano-emulsion comprising a CBFβ-RUNX1 inhibitor. The composition comprises a particle with a length of less than 200 nanometers in at least one dimension.

6 Claims, 18 Drawing Sheets

(56) References Cited

OTHER PUBLICATIONS

Wong et al., "Orbital Angiogenesis and Lymphangiogenesis in Thyroid Eye Disease: An Analysis of Vascular Growth Factors with Clinical Correlation," Ophthalmology, 2016, 123(9):2028-2036.

[No Author Listed], "Final Report on the Safety Assessment of Myristyl Myristate and Isopropyl Myristate," Journal of the American College of Toxicology, Jul. 1982, 1(4):55-80.

Elsevier's Encyclopedia of Food and Health, 1st ed., Caballero (ed.), Aug. 2015, pp. 498-502.

Elsevier's Food Enrichment with Omega-3 Fatty Acids, 1st ed., Jacobsen (ed.), Jul. 2013, Chapter 5, 44 pages.

Elsevier's Modifying Lipids for Use in Food, 1st ed., Gunstone (ed.), Sep. 2006, Chapter 16, 36 pages.

Elsevier's xPharm: The Comprehensive Pharmacology Reference, 1st ed., Enna (ed.), Jan. 2007, 3 pages.

Hedge et al., "Microemulsion: New Insights into the Ocular Drug Delivery," ISRN Pharmaceutics, Jun. 2013, 2013:1-11.

Kale et al., "Emulsion Micro Emulsion and Nano Emulsion: A Review," Systematic Reviews in Pharmacy, Nov. 2016, 8(1):39-47.

Okur et al., "Novel Ocular Drug Delivery Systems: An Update on Microemulsions," Journal of Ocular Pharmacology and Therapeutics, Jul. 2020, 36(6):342-354.

* cited by examiner

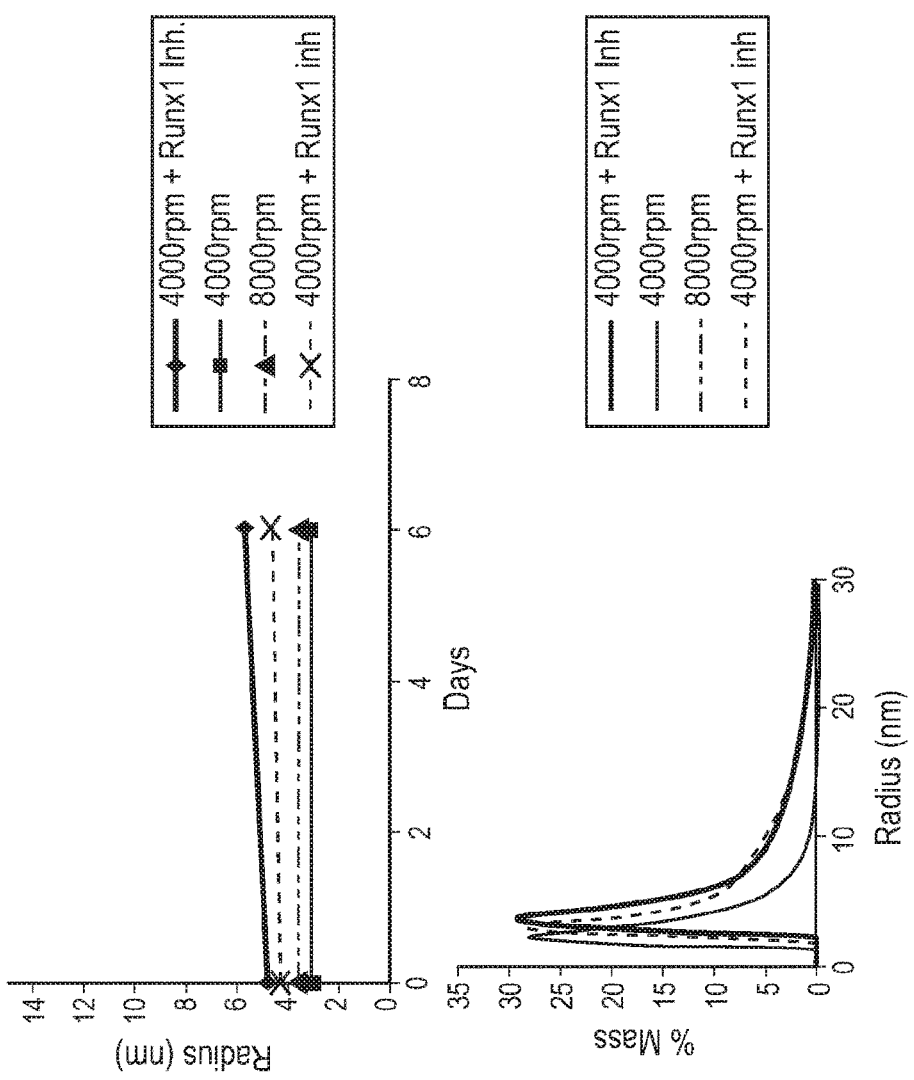
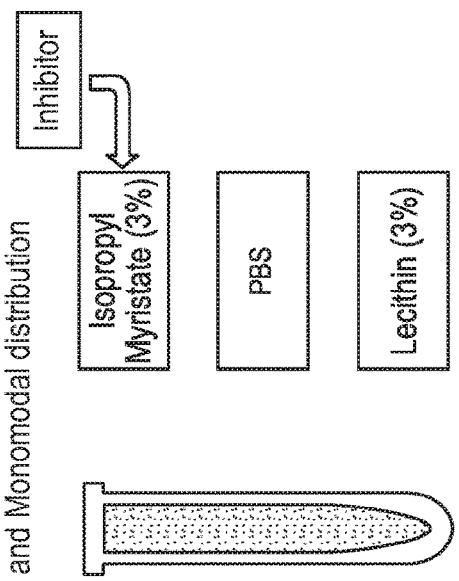
FIG. 4

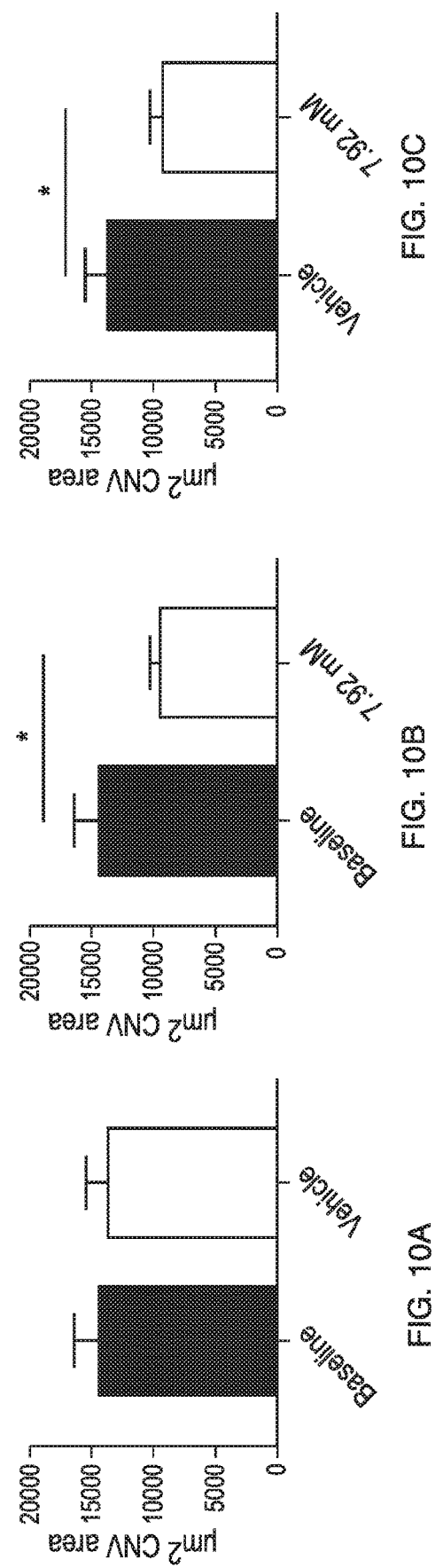

NANO-EMULSION OF CBFß-RUNX1 INHIBITOR FOR OCULAR DRUG DELIVERY

RELATED APPLICATIONS

This application is a U.S. national stage application filed under 35 U.S.C. § 371 of International Patent Application No. PCT/US18/61156, filed Nov. 14, 2018, which claims benefit of priority to U.S. Provisional Application No. 62/586,027, filed Nov. 14, 2017, the entire contents of which is incorporated herein by reference.

FIELD OF THE INVENTION

The present invention relates to formulations for ocular use.

BACKGROUND

The eye is a unique organ, both anatomically and physiologically. For example, the cornea and the crystalline lens are the only tissues in the body besides cartilage that have no blood supply, thus limiting the accessibility of these ocular structures for medications. Another example, as the eye is part of the central nervous system, there exists a blood retinal barrier analogous to the blood brain barrier that limits the accessibility of the eye to medications. The complexity of the eye provides unique challenges to drug delivery strategies.

SUMMARY OF THE INVENTION

The invention provides a solution to many problems and/or drawbacks of earlier ocular formulations and features a nano-emulsion composition, e.g., a nano-emulsion comprising a core binding factor β (CBFβ)-Runt-Related Transcription Factor 1 (RUNX1) (CBFβ-RUNX1) inhibitor. For example, Ro5-3335 has been difficult to formulate due to its i insoluble in aqueous solution, it is recommend that this chemical be solubilized in DMSO, which has known intraocular toxicity. In our experience and use of this chemical, we found that it immediately precipitates out of solution even when it is initially solubilized in DMSO, making the drug much less effective due to decreased availability of the drug. Our experiments in vitro show that the emulsified drug works much better than the insoluble drug. With our emulsion, we have devised a composition to encapsulate the drug in a nanonsphere, which allows for suspension in an aqueous solution, and increases availability of the drug, and also improves penetration of ocular tissues.

A CBFβ-RUNX1 inhibitor, e.g, Ro5-3335, modulates the Runx1-CBFβ heterodimer formation. For example, Ro5-3335 is a cell-permeable benzodiazepine that suppresses CBFα/Runx1-CBFβ transactivation activity via direct bindings to both subunits of the heterodimeric transcription factor complex, thereby reducing cell proliferation, e.g., the suppression/inhibition in turn reducing proliferation of retinal endothelial cells.

The nano-emulsion composition comprises a particle with a length of less than 200 nanometers in at least one dimension. For example, the particle comprises a substantially spherical shape and comprises a radius of less than 200 nanometers. An exemplary particle comprises a radius of less than 175, 150, 125, 100, 75, 50, 25, or 10 nanometers, e.g., a particle comprises a radius of 2-8 nanometers.

A CBFβ-RUNX1 inhibitor is encapsulated in the particle. For example, the inhibitor comprises Ro5-3335. In other examples, the inhibitor comprises 7-fluoro-1,3-dihydro-5-(1h-pyrrol-2y-yl)-2H-1,4-benzodiazepin-2-one, a fluorine analogue of R05-3335. Exemplary particles include inactive compounds (e.g., carriers or vehicle compounds) such as isopropyl myristate and/or lecithin. In other examples, an inactive vehicle compound include a scaffold material such as polycaprolactone (PCL).

The nano-emulsion formulations described herein are associated with numerous advantages for clinical applications. For example, the nano-emulsion formulations are particularly advantageous for use in treatment of an ocular disease/disorder such as aberrant ocular angiogenesis by topical administration such as eye drops. In another example, the formulation including a PCL scaffold may be applied to the ocular surface or implanted as a device inside the eye to achieve continuous drug release. This is particularly important as currently FDA approved modalities of treatment for aberrant angiogenesis including age-related macular degeneration, proliferative diabetic retinopathy, retinopathy require regularly scheduled intravitreal injections, which are onerous to the patients and carry the risks of intravitreal injections including infection, vitreous hemorrhage, and retinal detachment. Drug-PCL scaffolds in the form of nano particles or implantable devices may also be useful to achieve continuous drug release in situations of mass casualties or combat situations as means to temporize the eye and prevent further damage in situations where it is not practical or safe to continuously apply eye drops. The compositions and methods are also useful and advantageous as treatments for thyroid eye disease, aberrant corneal angiogenesis, and corneal graft rejection and other conditions characterized by aberrant scarring or healing such as corneal wounds and proliferative diabetic retinopathy may benefit from novel modalities of treatment based on topical applications.

The invention comprises two variations of a formulation: a nano-emulsion formulation and a dry powder or suspension thereof. The nano-emulsion formulation bypasses the need for intravitreal injections, which may have a risk of injection in some subjects. The nano-emulsion formulation also allows patients to administer drugs themselves at a lower cost. In a combat or a mass casualty setting, a nanoemulsion is provided and/or packaged in containers to facilitate easy and expedient use by medical professionals and lay persons, i.e., people with little or no medical training. The formulations are applied to the eye as a way to mitigate damage and temporize the eye until more sophisticated treatment options are available, e.g., after transport to a medical facility. A nanoemulsion could be administered by the patient, or someone with basic training in the military or a civilian population.

Also, within the invention is a method of making an emulsion comprising: contacting an active agent with an oil phase solvent in the presence of a liquid dispersion medium, wherein the liquid dispersion medium comprises water or an aqueous salt solution to provide a dispersion of the active agent, and mixing the dispersion with a surfactant under conditions to provide the emulsion having an average particle size of about 200 nm or less. For example, the oil phase solvent, e.g., a solvent comprising isopropyl myristate, is present in an amount from about 0.01% to about 100%, by total weight. The contacting step comprises grinding, homogenization, or sonication or other means of mixing the fractions together. In preferred embodiments, the active agent comprises a Runt-Related Transcription Factor 1

(RUNX1) small molecule inhibitor such as Ro5-3335. In other preferred examples, the RUNX1 inhibitor comprises 7-fluoro-1,3-dihydro-5-(1h-pyrrol-2y-yl)-2H-1,4-benzodiazepin-2-one.

Exemplary concentrations of the inhibitor range from a concentration from about 0.01 mM to about 10 mM. The emulsion composition optionally a surfactant such as propylene glycol, polyethylene glycol, or lecithin.

An exemplary method of preparing an emulsion comprises the following steps: a) preparing an aqueous solution, wherein the aqueous solution comprises an active agent, b) separately preparing a first polymer solution, wherein the first polymer comprises polycaprolactone (PCL), c) adding the aqueous solution to the first polymer solution to create an emulsion, and d) adding the emulsion prepared in c) to a second polymer solution, wherein the second polymer comprises polyvinyl alcohol, and homogenizing the emulsion. The method may optionally comprise steps of evaporating, centrifuging and lyophilizing the emulsion. Other optional steps may include coating the emulsion with gold or platinum.

The emulsion is useful to deliver active agents to bodily tissues such as ocular tissues. Such emulsions are useful to treat ocular disorders or diseases. For example, the emulsions comprise an active agent such as a CBFβ inhibitor, e.g., the agent binds to CBFβ and inhibits its binding to RUNX1. Alternatively, the agent binds to RUNX1, thereby inhibiting/reducing CBFβ-RUNX1 binding. In some examples, the emulsion comprises particles, and wherein the particles are about 200 nm in diameter or smaller in diameter, e.g., as described above.

Also, within the invention is a method of treating an ocular disorder or disease comprising administer to an ocular tissue of a subject the nano-emulsion or nano-particulate composition described herein. Ocular disorders or disease to be treated include Age-related macular degeneration (AMD), choroidal neovascularization (CNV), non-proliferative and proliferative diabetic retinopathy (DR) with or without diabetic macular edema (DME), retinal vein occlusions (RVO), retinopathy of prematurity (ROP), corneal angiogenesis, corneal graft rejection, neovascular glaucoma, a vascular malformation, a cavernous hemangioma, ocular ischemic syndrome, Coats' Disease, familial exudative vitreoretinopathy (FEVR), Norrie's Disease, Von Hippel-Lindau disease, or any condition that includes pathological angiogenesis as part of its biology. Such nano-emulsions are also useful for other proliferative ocular conditions such as: proliferative vitreoretinopathy (PVR), and ocular cancers (retinoblastoma, ocular lymphoma, melanoma, etc.). Other indications to be treated include thyroid eye disease, aberrant corneal angiogenesis, corneal epithelial down growth, and corneal graft rejection. Other disorders or diseases include those characterized by aberrant Epithelial-mesenchymal transition (EMT) or the reverse process MET (mesenchymal-epithelial transition) such as pathological ocular fibrosis and pathological ocular proliferation. Other exemplary conditions include glaucoma, a condition for which the pathobiology includes fibrosis of the trabecular mesh.

Formulation for administration include: Formulation 1 (emulsion) and Formulation 2 (lyophilized powder of polymer for sustained drug release upon suspension in physiological solution e.g. Balanced Salt Solution or in Phosphate Buffered Saline).

The first formulation is useful for administration of a Runx1 inhibitor as a topical ophthalmic in the form of eye drops. The advantage of this formulation is its ability to penetrate the ocular surface and allow for effective concentrations of the drug to the posterior segment of the eye and allows for administration to the front of the eye as well. Patients will be able to do this themselves at home and as needed depending on the severity of the disease or as a preventative measure according to the doctor instructions.

This formulation may be used in a civilian or military settings when patients have been stabilized and are ambulatory. This formulation bypasses the need for the use of intravitreal injections and can be useful for indications affecting any part of the eye.

Formulation 2 (lyophilized powder of polymer for sustained drug release upon suspension in physiological solution e.g. Balanced Salt Solution or in Phosphate Buffered Saline) may be used in two ways as follows. In a combat or mass casualty situation, a kit will contain the lyophilized particles in one compartment and a physiological solution in another and the kit has the capability of mixing the powder with the solution and administer on top of ocular structures that have suffered trauma. This could be done by the affected individuals or someone with minimal treatment with the goal in mind of temporizing the eye and prevent further damage until the soldier or mass casualties victims could be transported for additional treatment. The eye is then covered with a shield right after trauma and stays covered for many hours or days preventing administration of drugs via eye drops. In this case this sustained release formulation has unique advantages because they are applied onto the damaged ocular structure and release drug during the time the eye is covered and until further treatment is provided after transport.

In other situations, after trauma or retina detachment has occurred, a medical professional or surgeon may decide that after surgical repair has been completed the patient may benefit from receiving this formulation inside their eye in the vitreous cavity. In this situation, the patient will receiving treatment from the moment the surgery is completed and for an extended period of time throughout the post-operative period. The method is carried prior to, during, or after surgery.

An advantage of the invention is that the patient will not require subsequent intravitreal injections after the surgery which introduces additional risks associated with intravitreal injection. Another advantage is that the patient will not require subsequent intravitreal injections after the surgery which introduces additional risks associated with intravitreal injection.

This formulation can also be administered via intravitreal injections if necessary or via a subtenons depot. Alternatively, the composition is administered by spraying onto the eye or dropping onto the eye as a topical eye drop. In another example, the compostion is administered at the time of surgery, e.g., minutes before, during, or after surgery, e.g., before closure of the incision of the ocular surgery.

Each embodiment disclosed herein is contemplated as being applicable to each of the other disclosed embodiments. Thus, all combinations of the various elements described herein are within the scope of the invention.

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds, e.g., nucleic acid molecules, polynucleotides, polypeptides, proteins, or small molecules are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Similarly, a purified peptide or protein (e.g., identified by a specific amino acid sequence) is free of the amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice. The term "subject" as used herein includes a human as well as an animal such as a companion animal, e.g., dog or cat, as well as performance animals, e.g., horses such as race horses, as well as livestock animals, e.g., chickens, cattle, oxen, goats, or sheep.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject. An excipient is an inactive substance that serves as the vehicle or medium for a drug or other active substance.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Biopolymers" as used herein may refer to polymers that are produced by living organisms; they are "polymeric biomolecules" or "biodegradable polymer." Since they are polymers, biopolymers contain repeat monomeric units that are covalently bonded to form larger structures (i.e., linear biopolymers). Exemplary biopolymers may include cellulose, starch, lignin, chitin, and various polysaccharides. These materials and their derivatives offer a wide range of properties and applications. Natural polymers tend to be readily biodegradable, although the rate of degradation is generally inversely proportional to the extent of chemical modification. As described herein, the polymer comprises polycaprolactone (PCL). The term "linear biopolymer" as used herein may refer to polymers produced by living organisms (e.g., biopolymers) that are connected in a straight chain of repeat monomeric subunits.

The term "polymer" as referred to herein is meant as a macromolecule, composed of many repeated subunits called monomers. The word polymer designates an unspecified number of monomer units. When the number of monomers is very large, the compound is sometimes called a high polymer. Polymers are not restricted to monomers of the same chemical composition or molecular weight and structure. Some natural polymers are composed of one kind of monomer. Most natural and synthetic polymers, however, are made up of two or more different types of monomers.

Such polymers are known as copolymers. Polymers can be linear or branched. For example, a linear polymer characterized by a repetition of ester groups along the backbone chain is called a polyester.

Exemplary natural polymeric materials include shellac, amber, wool, silk, rubber, and cellulose. Non-natural (e.g., synthetic) polymers include synthetic rubber, phenol formaldehyde resin, neoprene, nylon, polyvinyl chloride, polystyrene, polyethylene, polypropylene, and silicone. Additional synthetic polymers that can be used include biodegradable polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, polyethylene oxide, polyvinyl alcohol, Teflon®, and nylon. A non-absorbable polyvinyl alcohol sponge is available commercially as Ivalon™, from Unipoint Industries.

"Emulsion" as used herein may include a fine dispersion of minute droplets of one liquid in another in which it is not soluble or miscible. Alternatively, "emulsion" may refer to a mixture of two or more liquids that are normally immiscible (unmixable or unbendable). Emulsions are part of a more general class of two-phase systems of matter called colloids.

"Patient," "subject," "patient in need thereof," and "subject in need thereof" are herein used interchangeably and refer to a living organism suffering from or prone to a disease or condition that can be treated by administration using the methods and compositions provided herein. Non limiting examples include humans, other mammals, bovines, rats, mice, dogs, monkeys, goat, sheep, cows, deer, and other non-mammalian animals. In some embodiments, a patient is human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may include 1 to 10, 1 to 20, 1 to 30, and 1 to 40 in one direction, or 50 to 40, 50 to 30, 50 to 20, and 50 to 10 in the other direction.

As used herein, "salts" or "salt form" or "pharmaceutically accepted salts" may include base addition salts (formed with free carboxyl or other anionic groups) which are derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts are formed as acid addition salts with any free cationic groups and generally are formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure may include amine salts formed by the protonation of an amino group with inorganic acids such as hydrochloric acid, hydrobromic acid, hydroiodic acid, sulfuric acid, phosphoric acid, and the like. Salts of the disclosure also include amine salts formed by the protonation of an amino group with suitable organic acids, such as p-toluenesulfonic acid, acetic acid, and the like. Additional excipients which are contemplated for use in the practice of the present disclosure are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference.

The term "solvent," as used herein, refers to a liquid solvent either aqueous or non-aqueous. The selection of the solvent depends notably on the solubility of the composition on said solvent and on the mode of administration. Aqueous solvent may consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol. As used herein, serum may be used as a solvent for reconstitution of the freeze-dried composition described herein.

The term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 ml of the component dissolved in a 100 ml of solvent. The term "weight/volume percent" or "% (w/v)" refers to a percentage of a component in a solution that is calculated on the basis of weight for the component and on the basis of volume for the solvent. For example, a 1.0% (w/v) solution of a component would have 1 g of the component dissolved in a 100 ml of solvent.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 4 is a series of line graphs showing the results of particle characterization following inhibitor encapsulation.

FIGS. 8A-D show CNV formation results after eNanoRo5 vs. eNano Vehicle treatment.

FIGS. 9A-C show quantification of CNV size after treatment.

FIG. 10A is a bar graph depicting CNV quantification validation. The data depict that no statistically significant differences were found between baseline (no treatment) and eNano Vehicle groups (P<0.8054).

FIG. 10B is a bar graph depicting CNV quantification validation, where statistically significant differences were found when the comparison was performed between eNanoRo5 and baseline. *P<0.0150. N=17 eyes (baseline and vehicle), N=16 eyes (eNanoRo5).

FIG. 10C is a bar graph depicting CNV quantification validation, where statistically significant differences were found when the comparison was performed between eNanoRo5 and eNano Vehicle. *P<0.0180. N=17 eyes (baseline and vehicle), N=16 eyes (eNanoRo5).

FIG. 11 shows a cell proliferation response to different treatment modalities in a model of PVR in rabbits.

DETAILED DESCRIPTION

Figure 1:
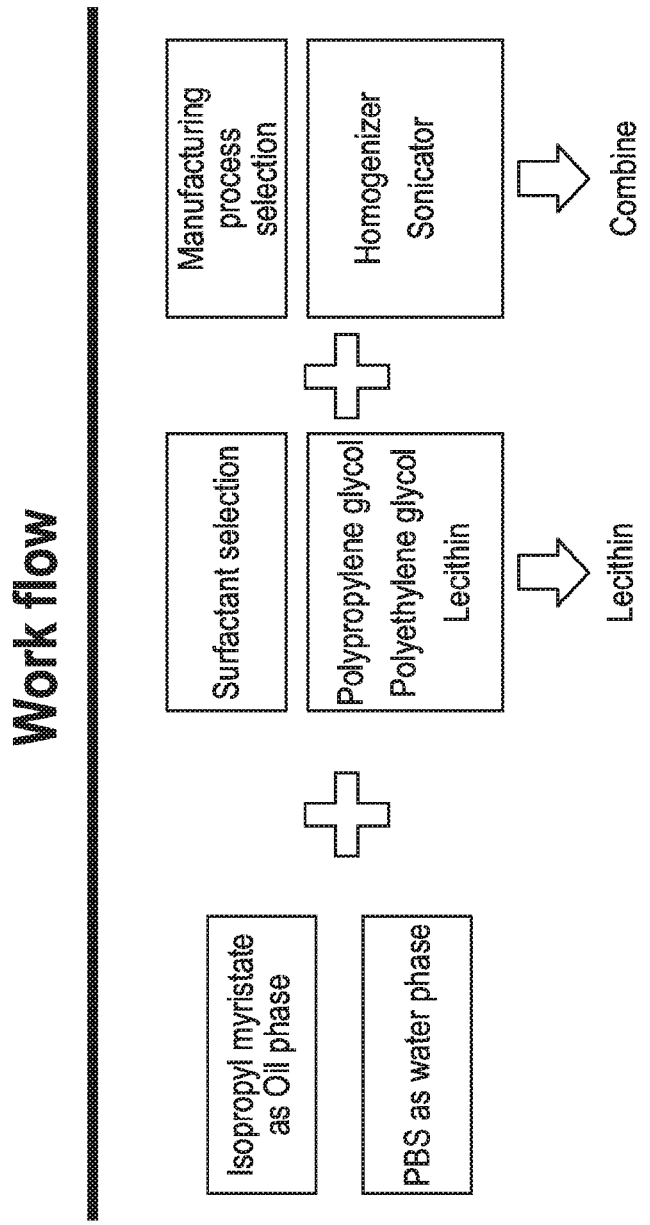
FIG. 1 is a diagram showing a nano-emulsion fabrication scheme.

Small molecule inhibitors of RUNX1 were fabricated into nano-emulsion formulations. For example, a RUNX1 inhibitor is encapsulated in nanoscale droplet/particles to form a nano-emulsion form of the inhibitor. Such nano-emulsions are useful for ocular drug delivery, e.g., to treat a number of pathologies including aberrant ocular angiogenesis. Age-related macular degeneration, choroidal neovascularization, non-proliferative and proliferative diabetic retinopathy (DR) with or without diabetic macular edema (DME), retinal vein occlusions (RVO), retinopathy of prematurity (ROP), corneal angiogenesis, corneal graft rejection, neovascular glaucoma, a vascular malformation, a cavernous hemangioma, ocular ischemic syndrome, Coats' Disease, familial exudative vitreoretinopathy (FEVR), Norrie's Disease, Von Hippel-Lindau disease, or any condition that includes pathological angiogenesis as part of its biology. Such nano-emulsions are also useful for other proliferative ocular conditions such as: proliferative vitreoretinopathy (PVR), and ocular cancers (retinoblastoma, ocular lymphoma, melanoma, etc.). Other indications to be treated include thyroid eye disease, aberrant corneal angiogenesis, corneal epithelial down growth, and corneal graft rejection (Syed Z. et al., Int Ophthalmol Clin. 2017 Fall; 57(4):31-38) as well as conditions characterized by aberrant scarring or healing such as corneal wounds and proliferative diabetic retinopathy (Wong, L. et al., Ophthalmology. 2016 Sep; 123(9):2028-36. Epub 2016 Jul 14. Orbital Angiogenesis and Lymphangiogenesis in Thyroid Eye Disease: An Analysis of Vascular Growth Factors with Clinical Correlation).

RUNX1 inhibitors have been developed and available for many years but a useful and safe application has been clinically useful. A limitation for the use of Runx1 inhibitors for cancer is that mutations resulting in either activation or inactivation have been found in individuals with blood cancer. Therefore there is a concern that a systemic administration of a RUNX1 inhibitors could cause severe side effects. Also RUNX1 plays critical roles in hematopoiesis and its systemic inhibition may affect this critical process. A surprising aspect of the invention is that the eye offers unique opportunities for the use of RUNX1 inhibition for clinical indications, because a RUNX1 inhibitor administered locally limiting its systemic effects. Also because of the immune privilege of the eye, the safety profile of RUNX1 inhibition in the eye may is more desirable than in other organs that are not immune privileged.

CBFβ and RUNX1 form a DNA-binding heterodimer. mall molecule drugs to CBFβ and inhibit its binding to RUNX (AI-10-47, AI-10-104, and AI-14-91). These drugs are know to bind CBF-β (Illendula A et al., Small Molecule Inhibitor of CBFbeta-RUNX Binding for RUNX Transcription Factor Driven Cancers. EBioMedicine. 2016; 8:117-131). Alternatively, the small molecule drug binds to RUNX1, thereby inhibiting/reducing CBFβ-RUNX1 binding. Alternatively, the small molecule can interfere with CBFβ-RUNX1 binding to DNA. Treatment with such inhibitors reduces binding of RUNX1 to target genes, thereby leading to the alteration of expression of RUNX1 target genes, which can in turn impact cell survival, differentiation, and/or function.

Polymers

In some examples, the methods described herein comprise preparing a polymer composition. The polymer comprises an active agent, e.g., a RUNX1 binding agent, a CBFβ binding agent, or an agent that binds to both CBFβ and RUNX1. In some examples, the agent binds to both CBFβ and RUNX1 such as a CBFβ-RUNX1 inhibitor. The polymer includes, for example, a biodegradable polymer, e.g., polycaprolactone (PCL). Additional biodegradable polymers widely used in the art include polyglycolic acid (PGA), polylactic acid (PLA), lactic acid-glycolic acid copolymer (PLGA), lactic acid-ε-caprolactone copolymer (PLCL), polydioxanone (PDO), polytrimethylene carbonate (PTMC), poly(amino acid), polyanhydride, polyorthoester, polyvinyl alcohol, and copolymers thereof. However, only PGA, PLA, and PLGA have been approved by the FDA as biodegradable polymers available for use in human body, and used as drug delivery microspheres and porous polymer scaffolds for tissue regeneration.

Polycaprolactone (PCL), (IUPAC name: (1,7)-Polyoxepan-2-one, Systematic IUPAC name (Poly(hexano-6-lactone); CAS Number: 24980-41-4; chemical formula: $(C_6H_{10}O_2)_n$), and other names include 2-Oxepanone homopolymer, and 6-Caprolactone polymer. PCL is a biodegradable polyester with a low melting point of around 60° C. and a glass transition temperature of about −60° C. The most common use of polycaprolactone is in the manufacture of specialty polyurethanes. Polycaprolactones impart good resistance to water, oil, solvent and chlorine to the polyurethane produced. PCL is often used as an additive for resins to improve their processing characteristics and their end use properties (e.g., impact resistance). Being compatible with a range of other materials, PCL can be mixed with starch to lower its cost and increase biodegradability or it can be added as a polymeric plasticizer to polyvinyl chloride (PVC).

In some examples, the composition (e.g., emulsion) includes salts or derivatives of PCL. Salts of PCL include organic and inorganic acid salts, for example, glutamate, lactate, citrate, hydrochloride, succinate, maleate, ascorbate, propionate, formate, carbonate and acetate salts. Derivatives of PCL include hydrophobically-modified PCL, succinyl PCL, carboxymethyl PCL, glycol PCL, sulfonated PCL, thiolated PCL or PCL modified with quaternary ammonium groups.

PCL has the following backbone chemical structure, wherein n represents any integer and represents the number of monomeric units in the PCL chain (e.g., the degree of polymerization).

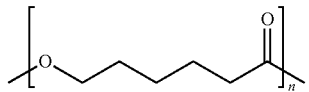

In examples, the composition (e.g., the emulsion) of the present disclosure includes PCL derivatives, for example, but is not limited to, esters, ethers or other derivatives formed by bonding acyl and/or alkyl groups with the hydroxyl groups. Additional examples of PCL derivatives include O-alkyl ethers of PCL and O-acyl esters of PCL. In embodiments, the composition of the present disclosure includes modified PCL, such as those conjugated to polyethylene glycol may be used in the present disclosure.

There are several known methods for preparing nanospheres by using such a biodegradable polymer, for example, a solvent evaporation-drying method (U.S. Pat. No. 4,652,441), a phase-separation method (U.S. Pat. No. 4,675,189), a spray-drying method (U.S. Pat. No. 6,709,650), a low temperature solvent extraction method (U.S. Pat. No. 5,019,400) and the like. For example, the method comprises a solvent extraction evaporation method.

The type of organic solvent used for dissolving the biodegradable polymer may vary according to the type of the polymer used and may include dichloromethane, methylene chloride, chloroform, carbon tetrachloride, acetone, dioxane, tetrahydrofuran, hexafluoroisopropanol and the like. For example, the organic solvent comprises dichloromethane (DCM). The biologically active material-containing polymer solution can be prepared by dissolving the biodegradable polymer and active agent in such an organic solvent at the same time. Alternatively, it can be prepared by dissolving the biodegradable polymer in the organic solvent in advance, and then dispersing the biologically active material therein.

In some examples, the composition of the present disclosure includes one or more polymers. For example, the polymer included in the composition includes a low molecular weight polymer or a high molecular weight polymer. Low molecular weight polymers may include for example, polymers less than 50 kDa, whereas high molecular weight polymers may include polymers greater than 100 kDa. In embodiments, the composition of the present disclosure includes ultra-high weight polymers, and may include polymers of greater than 1000 kDa. In embodiments, the molecular weight of the polymer is in a range from about 100 kDa to about 1200 kDa, from about 100 kDa to about 200 kDa, from about 100 kDa to about 300 kDa, from about 100 kDa to about 400 kDa, from about 100 kDa to about 500 kDa, from about 100 kDa to about 600 kDa, from about 100 kDa to about 700 kDa, from about 100 kDa to about 800 kDa, from about 100 kDa to about 900 kDa, from about 100 kDa to about 1000 kDa, from about 100 kDa to about 1100 kDa, from about 100 kDa to about 1200 kDa, and any weight there between.

The biodegradable polymer can be used in the amount of about 0.01% by weight to about 100% by weight, based on the total weight of the composition. In other examples, the polymer can be used in amount from about 0.01% by weight to about 90% by weight, from about 0.01% by weight, to about 80% by weight, from about 0.01% by weight to about 70% by weight, from about 0.01% by weight to about 60% by weight, from about 0.01% by weight to about 50% by weight, from about 0.01% by weight to about 40% by weight, from about 0.01% by weight to about 30% by weight, from about 0.01% by weight to about 20% by weight, from about 0.01% by weight, to about 10% by weight, from about 0.01% by weight to about 1% by weight, or from about 0.01% by weight to about 0.1% by weight.

Active Agent

Active agents include CBFβ-RUNX1 inhibitors for ocular drug delivery. In some examples, active agent can be used in the amount of about 0.01% by weight to about 100% by weight, based on the total weight of the composition. In other examples, the active agent can be used in amount from about 0.01% by weight to about 90% by weight, from about 0.01% by weight, to about 80% by weight, from about 0.01% by weight to about 70% by weight, from about 0.01% by weight to about 60% by weight, from about 0.01% by weight to about 50% by weight, from about 0.01% by weight to about 40% by weight, from about 0.01% by weight to about 30% by weight, from about 0.01% by weight to about 20% by weight, from about 0.01% by weight, to about 10% by weight, from about 0.01% by weight to about 1% by weight, or from about 0.01% by weight to about 0.1% by weight.

Alternatively, the active agent can be in a concentration from about 0.01 mM to about 100 mM. Other concentrations of the active agent comprise from about 0.01 mM to about 90 mM, from about 0.01 mM to about 80 mM, from about 0.01 mM to about 70 mM, from about 0.01 mM to about 60 mM, from about 0.01 mM to about 50 mM, from about 0.01 mM to about 40 mM, from about 0.01 mM to about 30 mM, from about 0.01 mM to about 20 mM, from about 0.01 mM to about 10 mM, from about 0.01 mM to about 5 mM, or from about 0.01 mM to about 1 mM.

By, "small molecule" may be referred to broadly as an organic, inorganic or organometallic compound with a low molecular weight compound (e.g., a molecular weight of less than about 2,000 Da or less than about 1,000 Da). The small molecule may have a molecular weight of less than about 2,000 Da, a molecular weight of less than about 1,500 Da, a molecular weight of less than about 1,000 Da, a molecular weight of less than about 900 Da, a molecular weight of less than about 800 Da, a molecular weight of less than about 700 Da, a molecular weight of less than about 600 Da, a molecular weight of less than about 500 Da, a molecular weight of less than about 400 Da, a molecular weight of less than about 300 Da, a molecular weight of less than about 200 Da, a molecular weight of less than about 100 Da, or a molecular weight of less than about 50 Da.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

pH of the Formulations

In examples, the present disclosure includes a composition (e.g., emulsion) including an active agent and one or more pH adjusting agents. The pH adjustment agent may be, for example, sodium hydroxide, hydrochloric acid, citric acid, malic acid, tartaric acid, acetic acid, phosphoric acid, maleic acid, glycine, sodium lactate, lactic acid, sodium citrate, ascorbic acid, sodium acetate, acetic acid, sodium bicarbonate, sodium carbonate, carbonic acid, sodium succinate, succinic acid, sodium benzoate, benzoic acid, sodium phosphates, tris(hydroxymethyl)aminomethane, histidine, histidine hydrochloride, or any combination(s) thereof.

Compounds useful as pH regulators include, but are not limited to include boric acid, sodium boric acid, sodium phosphate (including 1, 2 and 3 basic phosphate, such as 1 basic sodium phosphate 1 hydrate, 2 basic sodium phosphate 7 hydrate and mixtures thereof). Any other proper buffers can be used to stabilize the pH level of the ophthalmic liquid medicine by conferring physiological pH approved for ophthalmic liquid medicines. Since said buffers are just examples and these buffers are well known in ophthalmologic field, a person skilled in the art can choose proper buffers that can be used for the composition of the present disclosure.

In examples, the pH of the formulation is from about 2 to about 9. In other examples, the pH is in a range from about 3 to 9, or from about 4 to 9, or from about 5 to 9, or from about 6 to 9, or from about 7 to 9, or from about 8 to 9. In other examples, the pH is in a range from about 3 to 8, or from about 4 to 8, or from about 5 to 8, or from about 6 to 8, or from about 7 to 8. In exemplary embodiments, the pH is in a range from about 3.5 to about 7.5. Preferably, the formulation or solution for suspension/reconstitute or from about 3.5 to about 7.45.

Choroidal Neovascularization

Choroidal neovascularization (CNV) is the creation of new blood vessels in the choroid layer of the eye. Choroidal neovascularization is a common cause of neovascular degenerative maculopathy (i.e. 'wet' macular degeneration) commonly exacerbated by extreme myopia, malignant myopic degeneration, or age-related developments. CNV can occur rapidly in individuals with defects in Bruch's membrane, the innermost layer of the choroid. It is also associated with excessive amounts of vascular endothelial growth factor (VEGF). As well as in wet macular degeneration, CNV can also occur frequently with the rare genetic disease pseudoxanthoma elasticum and rarely with the more common optic disc drusen. CNV has also been associated with extreme myopia or malignant myopic degeneration, where in choroidal neovascularization occurs primarily in the presence of cracks within the retinal (specifically) macular tissue known as lacquer cracks. CNV can create a sudden deterioration of central vision, noticeable within a few weeks. Other symptoms which can occur include color disturbances, and metamorphopsia (distortions in which straight lines appears wavy). Hemorrhaging of the new blood vessels can accelerate the onset of symptoms of CNV. CNV may also include the feeling of pressure behind your eye.

CNV can be detected by using a type of perimetry called preferential hyperacuity perimetry. On the basis of fluorescein angiography, CNV may be described as classic or occult. Two other tests that help identify the condition include indocyanine green angiography and optical coherence tomography.

CNV is conventionally treated with intravitreal injections of angiogenesis inhibitors that block vascular endothelial growth factor or VEGF (also known as "anti-VEGF" drugs) to control neovascularization and reduce fluid accumulation within the retina, below the retina, or below the retinal pigment epithelium. Angiogenesis inhibitors include pegaptanib, ranibizumab, bevacizumab, and aflibercept (known by a variety of trade names, such as Macugen, Avastin, Lucentis, or Eylea). These inhibitors slow or stop the formation of new blood vessels (angiogenesis), typically by binding to or deactivating the transmission of vascular endothelial growth factor ('VEGF'), a signal protein produced by cells to stimulate formation of new blood vessels. The effectiveness of angiogenesis inhibitors has been shown to significantly improve visual prognosis with CNV, the recurrence rate for these neovascular areas remains high.

Encapsulation of such drugs and fabrication into nanoemulsion formulations are particularly useful for ocular administration.

Small Molecule CBFβ-RUNX1 Inhibitors

In various embodiments, the RUNX1 inhibitor is a small molecule inhibitor. Non-limiting examples include:

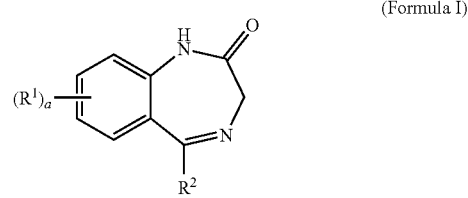

(Formula I)

or pharmaceutically acceptable salts or esters thereof, wherein each $R^1$ is individually selected from halogen, alkyl, aryl, heteroaryl, or alkoxy; $R^2$ is selected from aryl or heteroaryl; and a is 0 to 4;

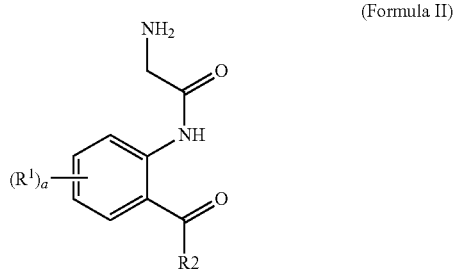

(Formula II)

or a pharmaceutically acceptable salt or ester thereof, wherein each $R^1$ is individually selected from halogen, alkyl, aryl, heteroaryl, or alkoxy; $R^2$ is selected from aryl or heteroaryl; and a is 0 to 4; or

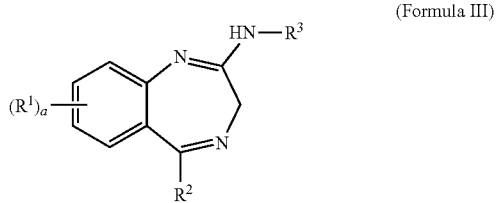

(Formula III)

or a pharmaceutically acceptable salt or ester thereof, wherein each $R^1$ is individually selected from halogen, alkyl, aryl, heteroaryl, or alkoxy; R2 is selected from aryl or heteroaryl; $R^3$ is alkyl or aryl; and a is 0 to 4.

In certain embodiments of formulae I-III, $R^2$ is a heteroaryl, particularly pyrrolyl, and especially pyrrol-2-yl. In certain embodiments of formulae I-III, $R^1$ is a halogen, particularly Cl or F. In certain embodiments of formula III, $R^3$ is a lower alkyl. In certain embodiments of formulae I-III, $R^2$ is a heteroaryl, particularly pyrrolyl, and especially pyrrol-2-yl; and $R^1$ is a halogen, particularly Cl or F. In certain embodiments of formula III, R2 is a heteroaryl, particularly pyrrolyl, and especially pyrrol-2-yl; $R^1$ is a halogen, particularly Cl or F; and $R^3$ is a lower alkyl.

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure —ROR, wherein R is an alkyl group.

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "derivative" refers to a compound or portion of a compound that is derived from or is theoretically derivable from a parent compound.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

Exemplary small molecule inhibitors include Ro5-3335, an analogue of Ro5-335 such as a fluorine-substituted analogue, e.g., 7-fluoro-1,3-dihydro-5-(1H-pyrrol-2-yl)-2H-1,4-benzodiazepin-2-one, Ro24-7429, NSC140873, MLS000548294, MLS001048862, or NSC156594. See, e.g., Cunningham et al. (2012) Proc Natl Acad Sci USA, 109(36): 14592-14597 and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141,735; 5,041,438; 5,036,101; and 3,405,122, as well as U.S. Patent Application Publication No. 2014/0004082, the entire contents of each of which are hereby incorporated herein by reference.

Ro5-3335 has the following structure:

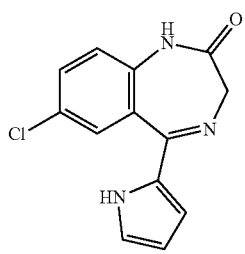 [SMILES: O=C1CN=C(c2ccc[nH]2)c2cc(Cl)ccc2N1]

The CAS Registry Number for Ro5-3335 is 30195-30-3.

Ro24-7429 has the following structure:

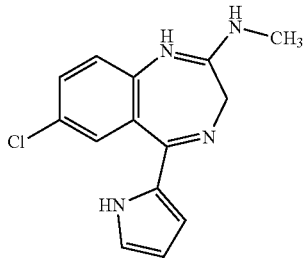

The CAS Registry Number for Ro24-7429 is 139339-45-0.

NSC140873 has the following structure:

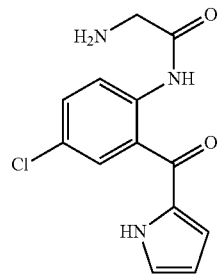 [SMILES: NCC(=O)Nc1ccc(Cl)cc1C(=O)c1ccc[nH]1]

The CAS Registry Number for NSC140873 is 106410-13-3.

MLS000548294 has the following structure:

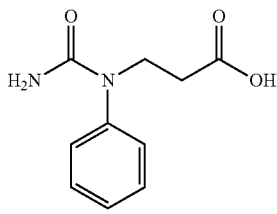 [SMILES: NC(=O)N(CCC(=O)O)c1ccccc1]

The PubChem ID for MLS000548294 is 768985.

MLS001048862 has the following structure:

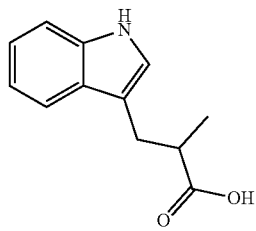

The PubChem ID for MLS001048862 is 2772042.

NSC156594 has the following structure:

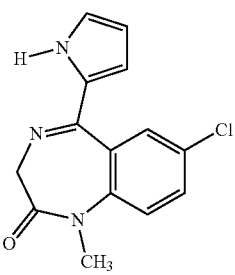 [SMILES: CN1C(=O)CN=C(c2ccc[nH]2)c2cc(Cl)ccc21]

The PubChem ID for NSC156594 is 457993.

The synthesis of several of the compounds disclosed above and analogs thereof have been previously described, for example, in U.S. Pat. Nos. 5,641,773; 5,164,376; 5,141,735; 5,041,438; 5,036,101; and 3,405,122, the entire contents of each of which are incorporated herein by reference.

In other examples, the RUNX1 inhibitor is 7-fluoro-1,3-dihydro-5-(1H-pyrrol-2-yl)-2H-1,4-benzodiazepin-2-one. 7-fluoro-1,3-dihydro-5-(1H-pyrrol-2-yl)-2H-1,4-benzodiazepin-2-one has the following structure, wherein the X is a fluorine (F) atom:

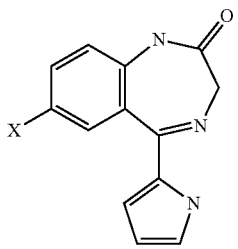

In some embodiments, the RUNX1 inhibitor inhibits RUNX1 via inhibition of CBFβ, which is the transcriptional partner of RUNX1.

Non-limiting examples of CBFβ inhibitors include:

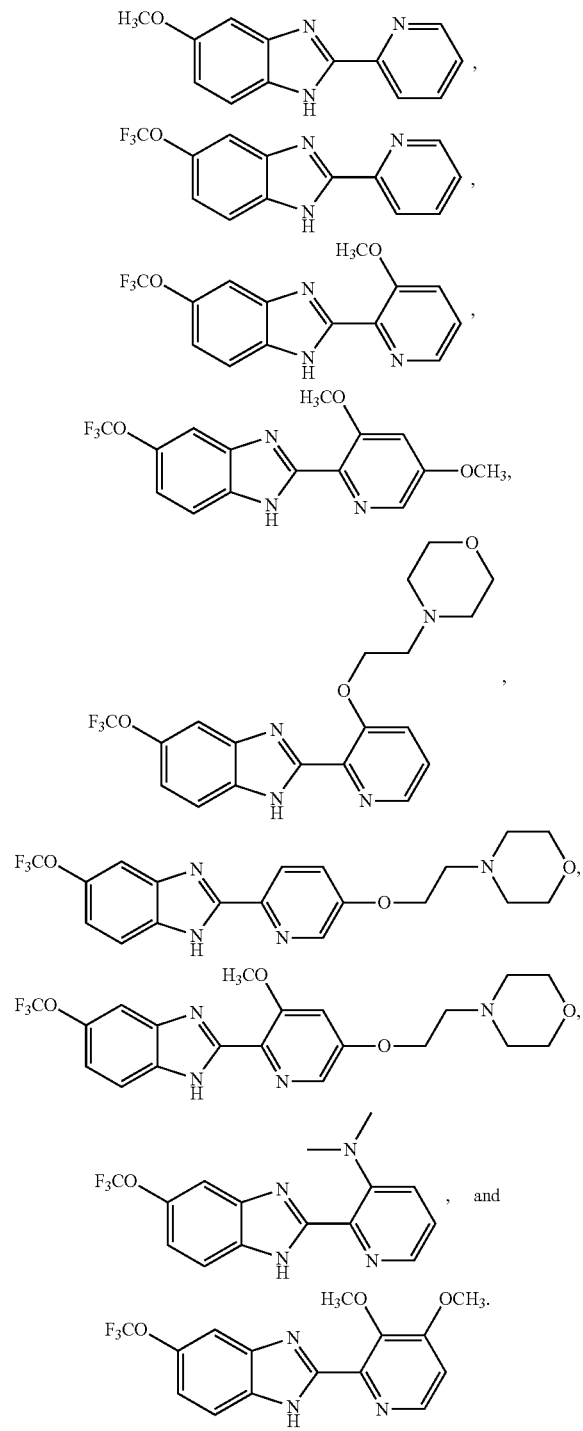

Non-limiting descriptions of CBFβ inhibitors and aspects thereof are described in Illendula et al. (2016) *EBioMedicine* 8: 117-131, the entire content of which is incorporated herein by reference. In some examples, the inhibitor comprises a pyridyl benzimidazole.

Topical Formulations

This formulation is part ideal for administration of a Runx1 inhibitor as a topical ophthalmic in the form of eye drops. The advantage of this formulation is its ability to penetrate the ocular surface and allow for effective concentrations of the drug to the posterior segment of the eye. Clearly, this allows for administration to the front of the eye as well. Patients will be able to do this themselves at home and as needed depending on the severity of the disease or as a preventative measure according to the doctor instructions.

This formulation may be used in a civilian or military settings when patients have been stabilized and are ambulatory.

This formulation bypasses the need for the use of intravitreal injections and can be useful for indications affecting any part of the eye.

Formulation 2 (lyophilized powder of polymer for sustained drug release upon suspension in physiological solution e.g. Balanced Salt Solution or in Phosphate Buffered Saline).

This formulation may be used in two ways as follows:

In a combat or mass casualty situation a kit will contain the lyophilized particles in one compartment and a physiological solution in another and the kit has the capability of mixing the powder with the solution and administer on top of ocular structures that have suffered trauma. This could be done by the affected individuals or someone with minimal treatment with the goal in mind of temporizing the eye and prevent further damage until the soldier or mass casualties victims could be transported for additional treatment. Usually the eye is covered with a shield right after trauma and stays covered for many hours or days preventing administration of drugs via eye drops. In this case this sustained release formulation has unique advantages because they are applied onto the damaged ocular structure and release drug during the time the eye is covered and until further treatment is provided after transport.

In other situations, after trauma or retina detachment has occurred, a surgeon may decided that after surgical repair has been completed the patient may benefit from receiving this formulation inside their eye in the vitreous cavity. In this the patient will be receiving treatment from the moment the surgery is completed and for an extended period of time throughout the post-operative period.

One advantage is that the patient will not require subsequent intravitreal injections after the surgery which introduces additional risks associated with intravitreal injection.

This formulation can also be administered via intravitreal injections if necessary or via a subtenons depot.

Kits

Kits, containers, packs, or dispensers containing drug-containing nano-emulsions or polymer particles together with instructions for administration, may be assembled. When supplied as a kit, the different components may be packaged in separate containers and mixed immediately before use, such as the components of the packaged emulsion or packaged polymer particles. Such packaging of the components separately may permit long-term storage without losing active component functions.

Kits may also include reagents in separate containers that facilitate the administration of the drug-containing compositions. The components of a kit are an emulsion, dry powder, or suspension for combining components for administration to a subject to be treated.

Containers or Vessels

Reagents included in kits can be supplied in containers of any sort such that the life of the different components are preserved and are not adsorbed or altered by the materials of the container. For example, sealed glass ampules may contain lyophilized hydrogels, or hydrogel components, or buffers that have been packaged under a neutral, non-reacting gas, such as nitrogen. Ampules may consist of any suitable material, such as glass, organic polymers (i.e., polycarbonate, polystyrene, etc.), ceramic, metal or any other material typically employed to hold reagents. Other examples of suitable containers include simple bottles that may be fabricated from similar substances as ampules, and envelopes that may have foil-lined interiors, such as aluminum or alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable or rupturable membrane that upon removal or rupture permits the components to mix. Removable membranes may be glass, plastic, rubber, etc.

Instructional Materials

Kits may also be supplied with instructional materials. Instructions may be printed on paper or other substrate and/or may be supplied as an electronic-readable medium, such as a floppy disc, CD-ROM, DVD-ROM, DVD, videotape, audio tape, etc. Detailed instructions may not be physically associated with the kit; instead, a user may be directed to an internet web site specified by the manufacturer or distributor of the kit, or supplied as electronic mail.

Example 1: Nano-Emulsion Fabrication Scheme

A fabrication scheme for producing CBFβ-RUNX1 inhibitor nano-emulsions is shown in FIG. 1. Different surfactant candidates were tested: Polypropylene glycol, Polyethylene glycol and Lecithin. The surfactants tested are approved by the Food and Drug Administration (FDA). Lecithin was chosen because it gives better phase behavior and drop size compared with the other possible surfactants (e.g., to achieve a particle size under 200 nm).

A nanoemulsion, e.g., eNanoRo5, was prepared by dispersion of Ro5-3335 in isopropyl myristate (oil phase) and mixed with PBS (water phase) by homogenizer×6 min×4000 rpm or 8000 rpm (pre-treatment) and, then exposed to Sonication×10 min×15 watts. The final concentration of Ro5-3335 in emulsion was 3.84 mM. The general fabrication scheme includes the following steps: dispersion of inhibitor in an oil phase; mixing the oil phase solution with a water phase solution; homogenization; and, sonication.

Example 2: Effect of Oil Phase Concentration and Processing Parameters

Different variables were studied to understand the drop size behavior. Studies were carried out to evaluate methodologies to get a drop size under 200 nm (this drop size dimension is considered an emulsion, i.e., nanoemulsion). First, the effect on the concentration of the oil phase in the drop size was studied, adding different amounts of isopropyl myristate (in which the inhibitor Ro5-3335 was dispersed) 1, 2 and 3% total volume. Then, the effect of the speed in the homogenizer step was also considered in the study, varying the velocity in 4000, 8000 and 10000 rpm.

Figure 2:
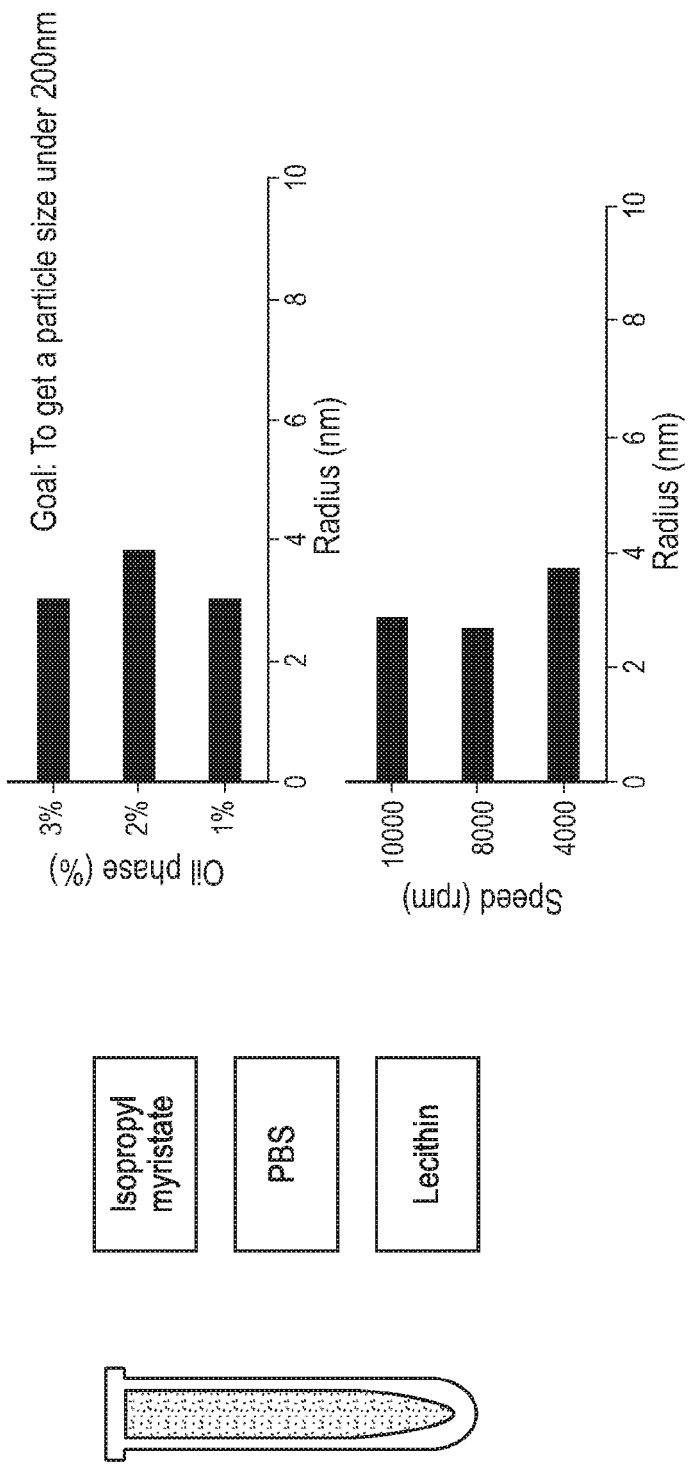
FIG. 2 is a bar graph showing the effect of oil phase concentration and processing parameters.

To measure the particle size of the emulsion, Dynamic Light Scattering (a technique in physics that can be used to determine the size distribution profile of small particles in suspension or polymers in solution) was used. Particle size was determined by measuring the random changes in the intensity of light scattered from a suspension or solution. FIG. 2 shows the effect of oil phase concentration and processing parameters.

The effect on the concentration of the oil phase in the drop size was determined. The test results indicated that there is no significant difference on the drop size for the different oil concentrations, indicating that it is possible to increase the amount of isopropyl myristate from 1 to 3%, to get more Ro5-3335 encapsulated in the emulsion.

The effect of the speed in the pre-treatment with the homogenizer was also determined. It seems to be a tendency/correlation for this variable (more speed led to smaller droplet size). However, 10000 rpm did not appear to be significantly different compared with 8000 rpm. For that reason, 4000 and 8000 rpm speeds were selected for the in vitro evaluation.

Example 3: Time Versus Drop Size

Figure 3:
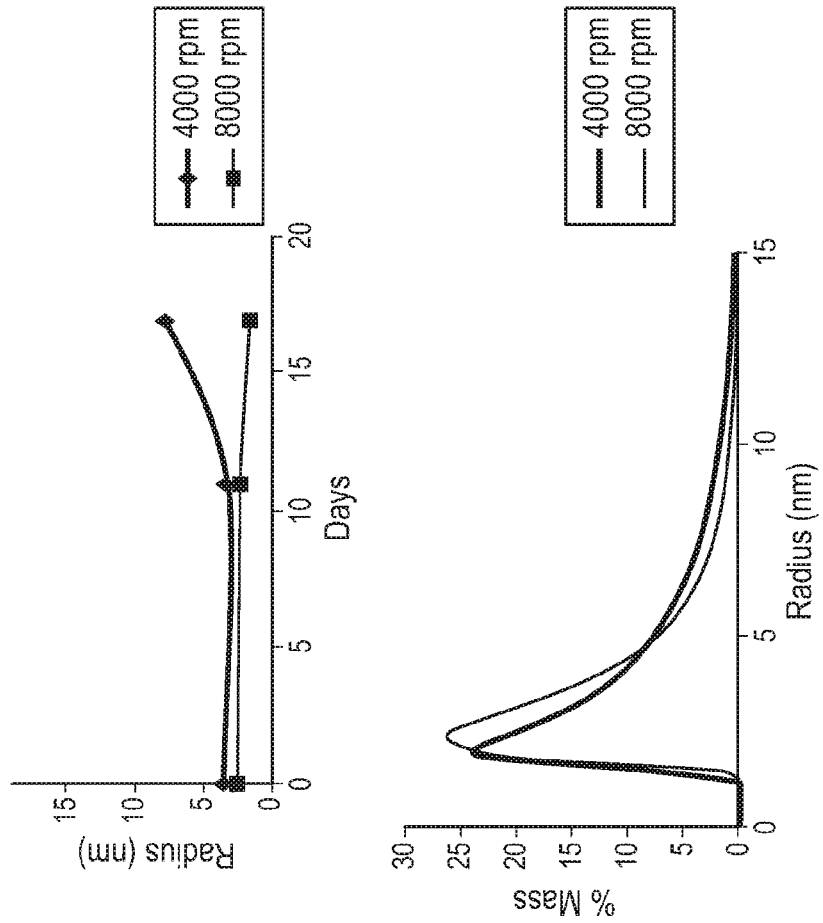
FIG. 3 is a series of line graphs showing time versus drop size.

Oil phase concentration at 3% was selected to prepare the emulsions. The emulsions (without Ro5-3335) were fabricated using 4000 rpm and 8000 rpm (for the homogenization step) were characterized for drop size for 17 days with Dynamic Light Scattering. Particle size distribution was also analyzed. FIG. 3 is a series of line graphs showing time versus drop size.

As time went by, there is a slightly change in drop size for both, 4000 rpm and 8000 rpm (around day 11). Nevertheless, drop size under 200 nm was still obtained, indicating that nanoemulsions were stable over time. A monomodal distribution was observed. A multimodal distribution was observed indicating homogeneity of the drops.

Example 4: Inhibitor Encapsulation

The Ro5-3335 inhibitor was encapsulated in the emulsion for 4000 rpm and 8000 rpm. The emulsions fabricated with and without the inhibitor, were characterized for drop size for 6 days with Dynamic Light Scattering. FIG. 4 shows results of inhibitor encapsulation.

Radius and mass were measured. The emulsions with the inhibitor for both speeds, were still in the nanoscale. There was a minimum change in drop size through time, although all of the tested samples were still characterized as nanoemulsions as far out as day 6. Subsequent analyses showed stability for at least 30 days. Samples were stored at 4° C.

The emulsions (with and without the inhibitor) for both speeds presented a monomodal particle size distribution.

Example 5: Effect on Cell Migration

The nanoemulsions were evaluated to determine their biological activity. Cell migration was assessed using a standard wound scratch assay as a model for angiogenesis. The scratch-wound assay is an art-recognized, reproducible assay commonly used to measure basic cell migration parameters such as speed, persistence, and polarity. Cells are grown to confluence and a thin "wound" introduced by scratching with a pipette tip. Cells at the wound edge polarise and migrate into the wound space. Human Retinal Microvascular Endothelial Cells (HRMECs) were analyzed for the ability to migrate into a wound area using the scratch wound assay. HRMEC's were primary cultures from Cell Systems.

Figure 5B:
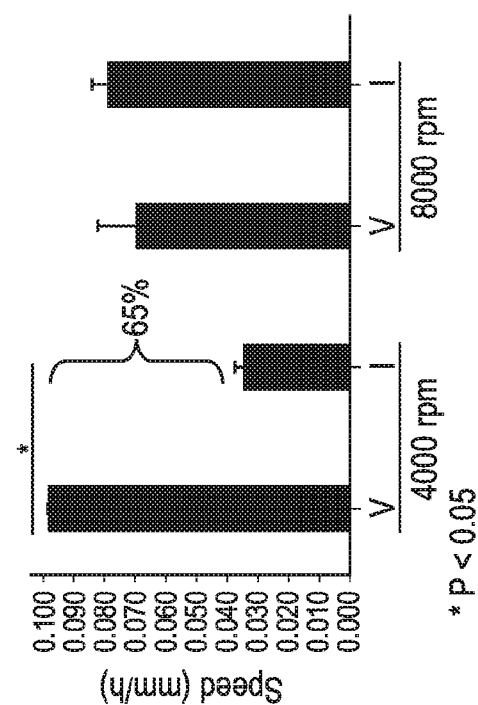
FIG. 5B is a bar graph showing the results of a cell migration assay.
Figure 5A:
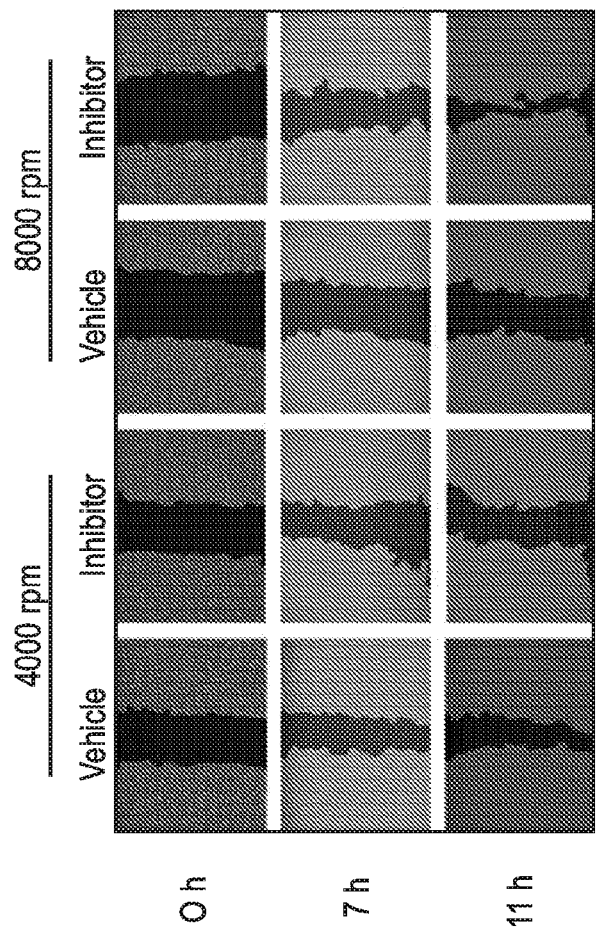
FIG. 5A is a photograph.
Figures 6A, 6B:
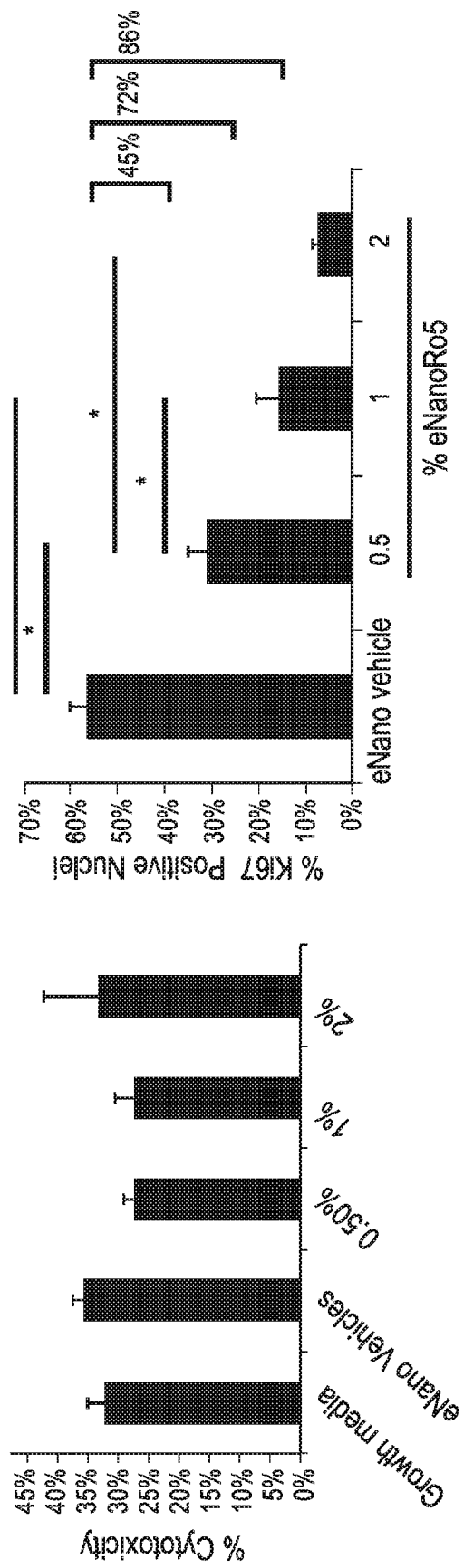
FIG. 6A is bar graph showing the cytotoxic effect of nano-emulsion (eNano), eNano Vehicle and eNanoRo5 over Human retinal endothelial cells (HRECs) through Lactate dehydrogenase quantification. Evaluation of eNano Vehicle and eNanoRo5 at three different concentrations (0.5, 1 and 2%) in the culture media. A non-cytotoxic effect of the nano-emulsions against complete growth media was observed. "eNanoRo5" or "eNanoRo5 emulsion" indicates RUNX1 inhibitor emulsion, and "eNano Vehicle" depicts emulsion without inhibitor.
FIG. 6B is a bar graph showing three different concentrations of the eNanoRo5 emulsion tested for proliferation assay (0.5, 1 and 2% concentrations) and compared with the emulsion vehicle. HRECs were treated for the vehicle and eNanoRo5 for 48 hours before proliferation assay. The antibody Ki67 was used as a proliferation marker. The cells were imaged on an EVOS® system. Image J were used for image analysis. A 45%, 72% and 86% reduction in cell migration in HRECs treated with the eNanoRo5 emulsion (for 0.5, 1 and 2% respectively) compared with the DMSO control was observed.
Figure 7A:
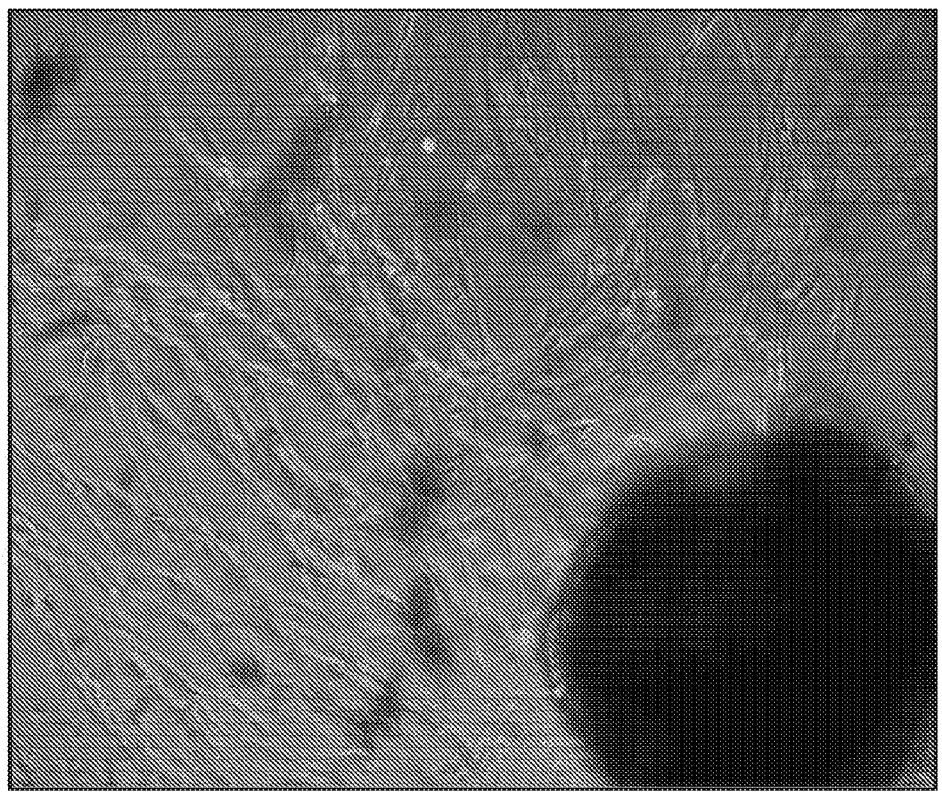
FIG. 7A is an image depicting eNanoRo5 (RUNX1 inhibitor, Ro5-3335, emulsion) preparation that reduced growth of human PVR membranes in an explant model at day 21 before treatment.
Figure 7B:
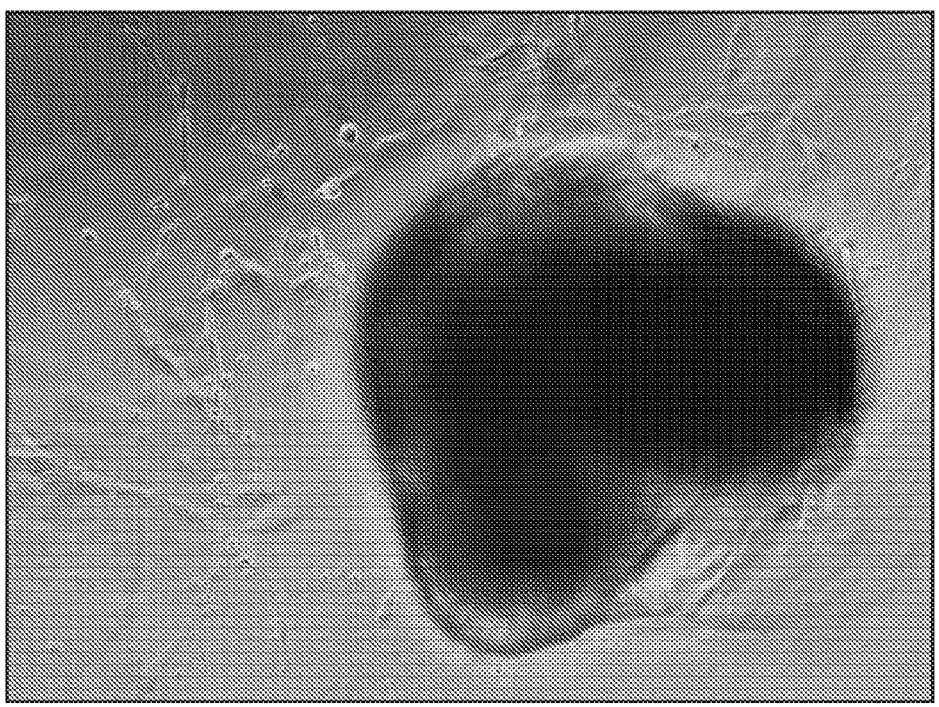
FIG. 7B is an image depicting eNanoRo5 emulsion preparation that reduced growth of human PVR membranes in an explant model at day 21 after treatment. A faster regression of the branches and apoptosis was observed in human PVR explants treated with RUNX1 inhibitor prepared as an emulsion. Detachment of the branches from the primary tissue was also observed.

One scratch was done per well. The cells were imaged on an EVOS® system every three hours for 11 h. Tscratch Matlab Module were used for image analysis. FIG. 5A is a photograph and FIG. 5B is a bar graph showing the results of a migration assay.

For the emulsion prepared at 4000 rpm, there was a 65% reduction in cell migration in HRECs treated with the inhibitor compared with the vehicle (DMSO). This indicates that a method of fabrication using 4000 rpm produced an effective emulsion preparation under the conditions used. In some examples, the emulsion is prepared/fabricated using various homogenizer speeds, e.g., 1000; 2000; 3000; 4000; 5000; 6000; 7000; 8000; 9000; 10,000; 11,000; 12,000 rpm or more. Optionally, processing at higher velocities such as speeds greater than 5000 rpm, e.g., 8000 rpm or faster is carried out with cooling such as on ice or in a refrigerated chamber to preserve biologic activity of the inhibitor.

Example 6: PCL Particle Method of Manufacture and In Vitro Testing

Polycaprolactone (PCL) Particle Procedure

Particles/spheres comprising nanoparticles or nanospheres for slow e.g., drug containing polymer particles were prepared using a double-emulsion protocol. The nanospheres (e.g., nanoparticles), for example, PCL nanospheres, were prepared with an oil-in-water emulsion (o/w) and solvent extraction evaporation.

Materials

| Chemical | Supplier | Catalog Number |
| --- | --- | --- |
| PCL (polycaprolactone) Mn = 45,000 | Sigma-Aldrich | 704105-100G |
| PVA (Poly vinyl alcohol) MW - 31,000-50,000 | Sigma-Aldrich | 363138-25G |
| DCM (Dichloromethane) | Sigma-Aldrich | D65100-1L |
| Trehalose | Sigma-Aldrich | PHR1344 |
| CBFβ-RUNX1 Inhibitor II, Ro5-3335 | Millipore Sigma | 219506-10MG |
| Ethyl alcohol, pure | Sigma-Aldrich | 459844-1L |

PCL Nanospheres: Oil-In-Water (O/W) Emulsion and Solvent Extraction Evaporation Technique (90:10 Polymer/Drug Ratio)

1. Dissolve 10 mg of Ro5 (Ro5-3335) into 300 μL of ethanol.
2. In a 50 mL Falcon tube, dissolve 100 mg of PCL into 5 mL of dichloromethane (e.g., by gentle mixing).
3. Once the PCL is completely dissolved, add the drug into the polymer solution.
4. Sonicate to emulsify the drug with the polymer 3 times at 200 W (using an ice bath); each of the sonications should last about 10 seconds.
5. Add the solution dropwise with a Pasteur pipette into 10 mL of a 1% w/v PVA solution while vortexing the suspension in a 50 mL centrifuge tube. Continue vortexing for an additional 15 seconds.
6. Immediately transfer the emulsified polymer to the sonicator. Sonicate the emulsion in three 10 sec bursts at 500 W (do not touch the probe sides or bottom of the test tube). Pause between each 10-second sonication to allow the solution to cool before proceeding. Perform this step using an ice bath.
7. Transfer o/w primary emulsion (e.g., the emulsion prepared in step 4) at a rate of 2 mL/min into 50 mL of a 0.5% w/v PVA solution; stir the solution at 600 rpm.
8. Homogenize the emulsion at 4000 rpm for 10 min.
9. Allow evaporation of the organic solvent over night by stirring, cover the beaker with aluminum foil.
10. Place the emulsion into two centrifuge tubes (e.g. to counterbalance) and centrifuge the dispersion at for 5000 rpm 30 min.
11. Add 5 mL of distilled water into each centrifuge tube and use vortex to suspend the nanoparticles.
12. Add 10 mL of distilled water and centrifuge at 17000 rpm for 15 min (repeat steps 9 and 10 three times).

Nanoparticle (NP) Lyophilization

1. Add a 1:2 trehalose:polymer (20 mg of trehalose) as cryoprotectant.
2. Transfer the nanoparticles to a pre-weighed 5 mL centrifuge tube and freeze at −80° C. for at least 30 min. Freeze for less than about 60 minutes to prevent water crystals from breaking the particles.
3. Moving quickly so as not to let the frozen contents melt, uncap the tube and cover the top with parafilm. (If any melting occurs, refreeze before placing in the lyophilizer)
4. Lyophilize for 48 hours.
5. Store lyophilized particles at −80° C. Storage at least at one month retained activity.

In Vitro PCL Particle Testing

Figure 12:
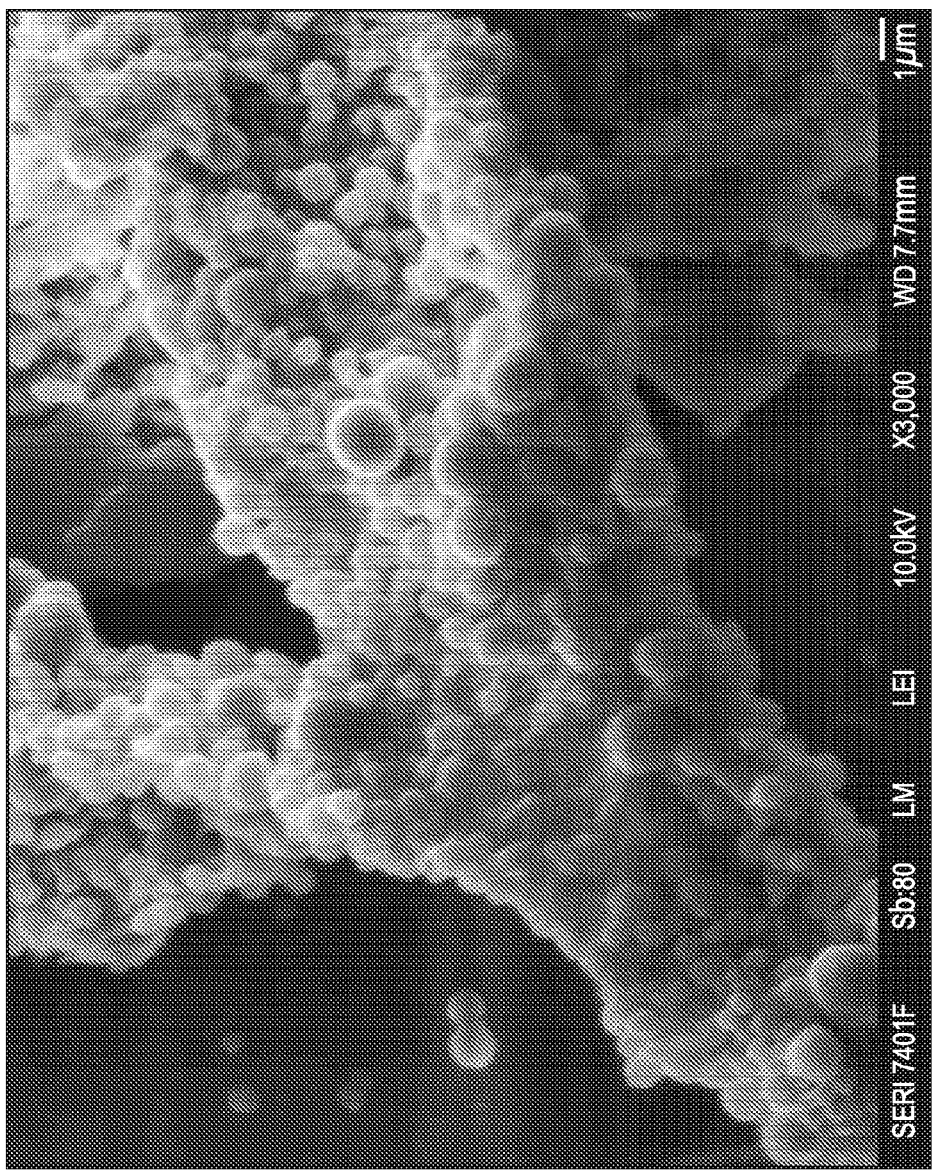
FIG. 12 is an image depicting the representative morphology of Ro5-3335-loaded Polycaprolactone (PCL) nanoparticles (eNanoRo5) visualized by Scanning Electron Microscopy (10 kV, ×3000). Scanning Electron Microscopy (SEM) was performed using a JEOL 7401F Field Emission Electron Microscope (JEOL USA, Inc.). Samples were coated with 10 nm gold/platinum layer. SEM analysis was employed to observe the morphology of the nanoparticles.

The nanoparticles prepared using the methodology described herein were visualized using electron microscopy (FIG. 12). The representative morphology of Ro5-3335-loaded PCL nanoparticles (as prepared by the method described herein) were visualized us scanning electron microscopy (10 kV, ×3000). The SEM was performed using a JEOL 7401F Field Emission Electron Microscope (JEOL USA, Inc.). Samples were coated with 10 nm gold/platinum layer. SEM analysis was employed to observe the morphology of the nanoparticles. The morphology of the Ro5-3335-loaded PCL nanoparticle shows clusters of spherical nanoparticles of various sizes. The image showed that a significant population of the particles had particles of a nano scale. It also showed that all the particles were rounded and that there were no fibers, which is the desirable structure. The image also showed the uniformity of shape.

Figure 13:
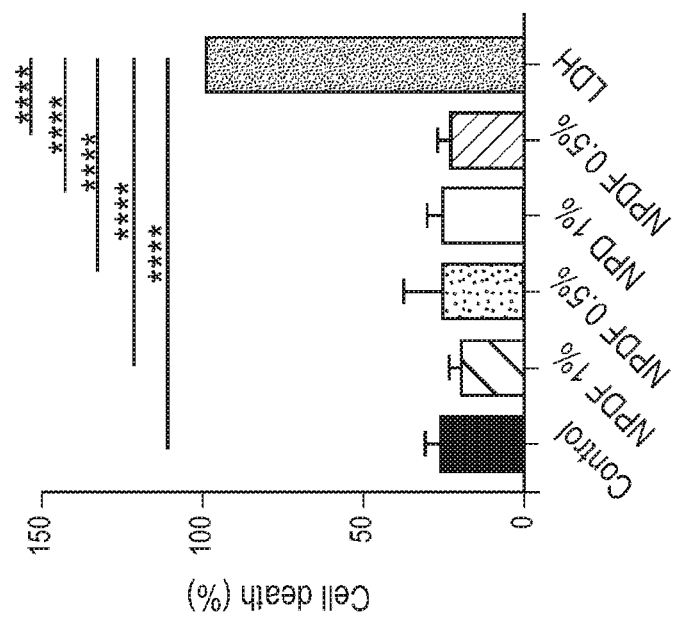
FIG. 13 is a bar graph depicting the cytotoxicity evaluated by a lactose dehydrogenase (LDH) assay of NPD and NPDF at different concentrations in human retinal microvascular endothelial cells (HRECS) after incubation for 48 h. Data represent mean±standard deviation, n=3 (****$p<0.0001$). NPD: NanoParticles Drug-loaded (drug—Ro5-3335), NPDF: NanoParticles Drug-Free.

The cytotoxicity (FIG. 13) and cell proliferation (FIG. 14) of the nanoparticles prepared using the methodology described herein were also evaluated. The cytotoxicity was evaluated using a lactate dehydrogenase (LDH) assay of nanoparticle drug-loaded (NPD, loaded with Ro5-3335) and nanoparticle drug-free (NPDF) samples, at different concentrations in human retinal endothelial cells (HRECS) after incubation for 48 h. HRECS ($1\times10^4$ cells per well) were cultured in 96-well plates in 100 μL of endothelial cell growth media 2 (EGM-2) supplemented with 2% fetal bovine serum (FBS) per well and maintained at 37° C. and 5% carbon dioxide ($CO_2$). NPDF and NPD were sterilized under ultraviolet (UV) light for 30 min and dispersed in media. Confluent cells were exposed to different concentrations of these samples for 48 h. After the exposure period, the media was removed and centrifuged at 4000 rpm for 5 min. 100 μL of the supernatant was collected and added to the substrate solution, and the absorbance at 340 nm was measured using a microplate reader. The absorbance of the test sample was normalized to the negative control and the results were expressed as percentage cell death. These analysis showed that the nanoparticles were not toxic to human retinal endothelial cells, as compared to controls (FIG. 13).

Figure 14:
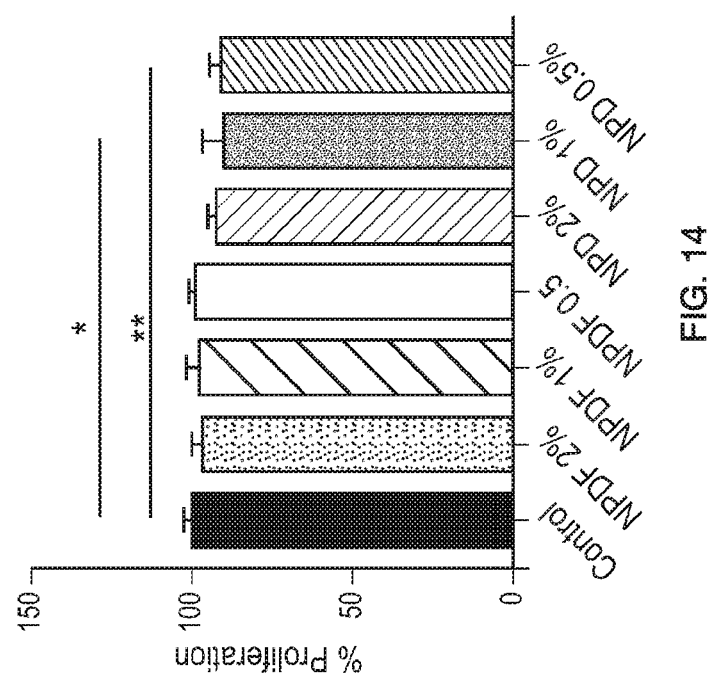
FIG. 14 is a bar graph depicting results of a cell proliferation assay evaluated by a CyQUANT Labeling kit of NPD and NPDF at different concentrations in HRECS cells after incubation for 48 h. Data represent mean±standard deviation, n=3 (*$p<0.1$, **$p<0.01$). NPD: NanoParticles loaded with a small molecule RUNX1 inhibitor (Ro5-3335), NPDF: NanoParticles Drug-Free. This data showed that Ro5-3335 loaded into PCL nanoparticles reduced the proliferation of HRECs.

The cell proliferation of the nanoparticles prepared using the methodology described herein were was also evaluated (FIG. 14). The cell proliferation was evaluated using a CyQUANT Labeling kit of NPD (nanoparticles loaded with a small molecule Runx1 inhibitor (Ro5-3335)) and NPDF at different concentrations in HRECS cells after incubation for 48 h. HRECS ($1 \times 10^4$ cells per well) were seeded in 96-well plates and cultured in 100 μL of EGM-2 supplemented with 2% FBS, and maintained at 37° C. in 5% $CO_2$ atmosphere. NPDF and NPD were sterilized under UV light for 30 min and dispersed in media, cells were treated with different concentrations of these samples for 48 h. Cell proliferation was assessed using a CyQuant Labeling kit. The medium without treatment served as control. Briefly, the culture medium was washed three times with phosphate buffered saline (PBS) and the cells were incubated with 100 μL of growth media for 1 h. Then, 3 mL of the growth medium was added with 12 μL of CyQuant Direct nucleic acid stain and 60 μL of CyQuant Direct Background suppressor I. 100 μL of the described solution was added to each well. Cells were incubated with the detection reagent for 60 min at 37° C. and the absorbance was measured at 480 nm using a microplate reader. The absorbance of the test sample was normalized to the control and the results were expressed as percentage cell proliferation. This data showed that Ro5-3335 loaded into PCL nanoparticles reduced the proliferation of HRECs.

Figures 8A, 8B, 8C, 8D:
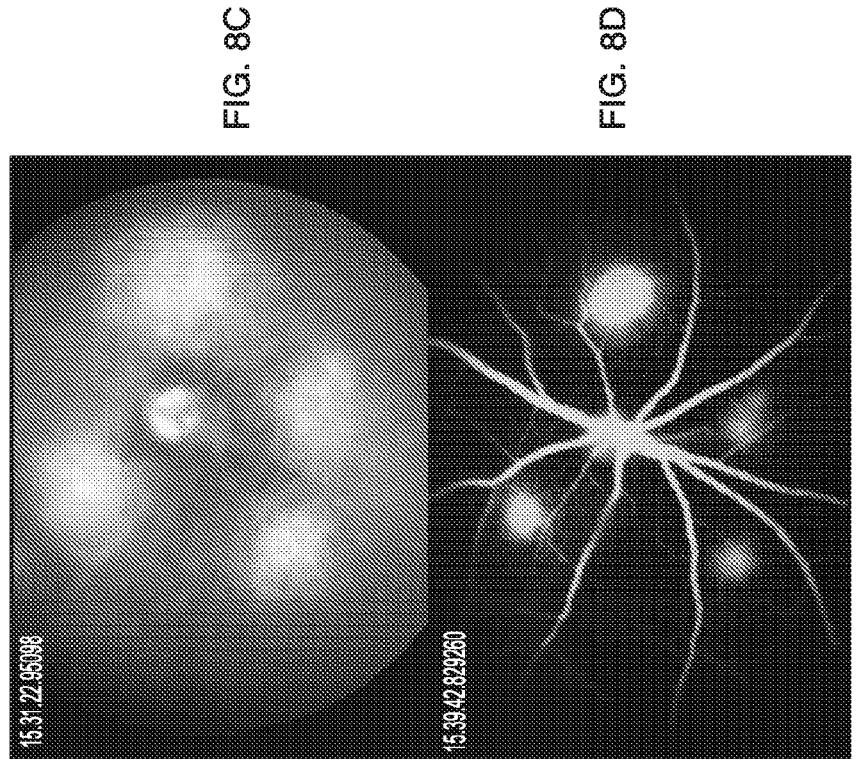
FIG. 8A is an image depicting that choroidal neovascularization (CNV) formation resulted after eNANO (eNanoRo5 (RUNX1 inhibitor, Ro5-3335, emulsion)) treatment. A funduscopic image was depicted 6 days after CNV laser induction in mice, and laser spots were identified.
FIG. 8B is an image depicting that CNV formation resulted after eNanoRo5 treatment. A funduscopic image was depicted 6 days after CNV laser induction in mice, and laser spots were identified. A representative image of fluorescein angiography, where differences in CNV formation and leakage is shown.
FIG. 8C is an image depicting CNV formation after eNano Vehicle treatment. A funduscopic image was depicted 6 days after CNV laser induction in mice, and laser spots were identified.
FIG. 8D is an image depicting that CNV formation resulted after eNano Vehicle treatment. A funduscopic image was depicted 6 days after CNV laser induction in mice, and laser spots were identified. A representative image of fluorescein angiography, where differences in CNV formation and leakage is shown.

Example 7: In Vivo Efficacy of Emulsion on Aberrant Angiogenesis in a Laser-Induced Mouse Model of Choroidal Neovascularization Choroidal Neovascularization (CNV) Formation Resulted after eNanoRo5 as Compared to eNano Vehicle Choroidal neovascularization (CNV) formation resulted after eNanoRo5 (e.g., a described herein with isopropyl myristate) treatment as compared to eNano Vehicle treatment (FIG. 8A-FIG. 8D). Funduscopic images were taken 6 days after CNV laser induction in mice. Representative images of fluorescein angiography where differences in CNV formation and leakage are depicted. These images showed a significant decrease in fluorescein leakage, as well as a decrease in the size of the CNV lesion with eNanoRo5 treatment as depicted in FIG. 8C when compared against FIG. 8D.

Figures 9A, 9B:
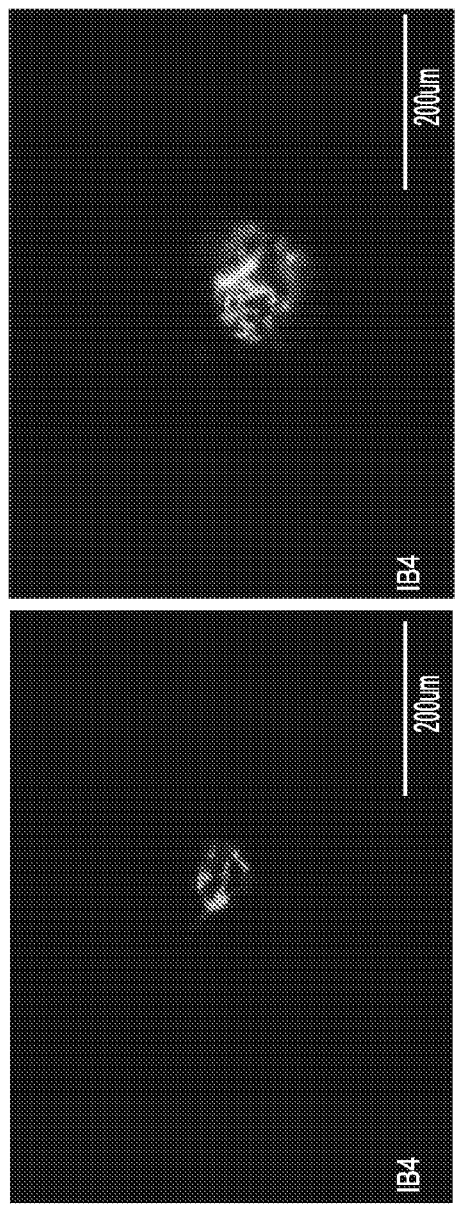
FIG. 9A is an image depicting the quantification of CNV size after treatment. The image depicts the eNanoRo5 group (n=16 eyes). The image also depicts the isolectin BR (IB4) staining of labeling the neovascular complex in a laser-induced CNV model in mice.
FIG. 9B is an image depicting the quantification of CNV size after treatment. The image depicts the vehicle group (n=17 eyes). A representative image of IB4 staining of labeling the neovascular complex in a laser-induced CNV model in mice is shown.
Figure 9C:
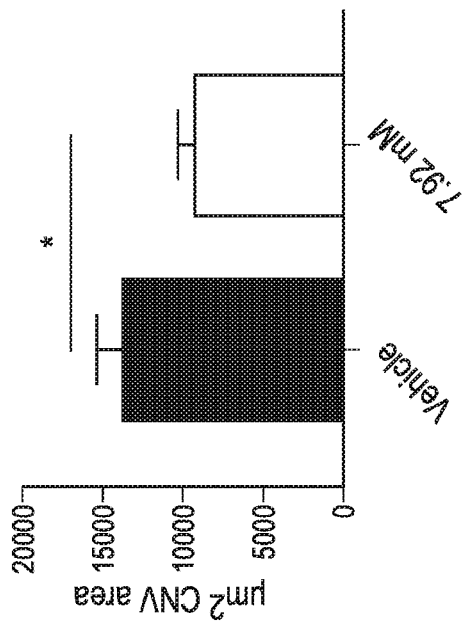
FIG. 9C is a bar graph depicting the quantification results of CNV area 7 days after laser induction. *P<0.0180.

The quantification of CNV size after treatment was also evaluated (FIG. 9A, FIG. 9B, and FIG. 9C). After 7 days, quantification results of CNV area after laser induction were determined. Higher magnification of the CNV lesions showed that there was a significant decrease in the size of the CNV lesion with eNanoRo5 treatment (FIG. 9A) when compared to eNano Vehicle control (FIG. 9B).

The results were further validated by including a non-intervention group (e.g., a baseline group) into the analysis (FIG. 10A, FIG. 10B, and FIG. 10C). Although there was no significant difference between the baseline and the vehicle group, a statistically significant difference was seen between a comparison of eNanoRo5 either baseline or vehicle. The data showed that there was no difference in the size of the CNV lesion between the eNano Vehicle group and an untreated baseline control (FIG. 10A). There was a significant decrease in the size of the CNV between the eNanoRo5 group and the untreated baseline control (FIG. 10B). Similarly, there was a significant decrease in the size of the CNV lesion between the eNanoRo5 group and the eNano Vehicle control (FIG. 10C). Topical administration of eNanoRo5 resulted in a significant decrease in the size of the CNV lesion in a laser-induced mouse model of CNV.

Methods

Animals

C57BL/6J male mice of 6-7-week-old purchased from Jackson Laboratories (Bar Harbor, Me.) were used. For all procedures, mice were anesthetized by intraperitoneal injection of Ketamine/Xylazine mixture (100/50 mg/kg) (KetaVed®, Vedco Inc., St. Joseph, Mo., USA/Anased®, Akorn Animal Health, Lake Forest, Ill.) and pupils were dilated by topical application of 1% Tropicamide drops (Bausch and Lomb Inc., Tampa, Fla.). Animals were maintained in a temperature-controlled, 12-hour day-night cycle environment with food and water ad libitum. Samples were collected after euthanasia in $CO_2$ chamber. Animal welfare regulation and experimental procedures were reviewed and performed in accordance with MEE Institutional Animal Care and Use Committee regulation, and followed the guidelines for the Use of Animals in Ophthalmic and Vision Research of the Association for Research in Vision and Ophthalmology.

Laser CNV Model

For the induction of CNV, laser photocoagulation was performed with a 532-nm laser (Merilas laser, Meridian, Thun, Switzerland) attached to Micron III image-guide system (Phoenix Research Labs, Pleasanton, Calif.) using 120 mW of power, duration of 50 ms and a spot size of 50 μm. Optimal alignment and focus of the eye with the camera was achieved for all the procedures to induce consistent and reliable laser photocoagulation. Four laser spots were performed at the 3, 6, 9 and 12 o'clock meridians, approximately at two or three disc diameters of distance from the optic nerve. Disruption of Bruch's membrane was confirmed by the appearance of a cavitation bubble at the site of the laser photocoagulation. Laser spots that did not result in the formation of a bubble were excluded from the studies.

Fluorescein Angiography

Fluorescein angiography was performed 6 days after laser induction. Under anesthesia, pupils were dilated with 1% Tropicamide drops (Bausch and Lomb Inc., Tampa, Fla.) and Genteal gel (Alcon, Forth Worth, Tex.) was applied as an optical contact and lubricant. Then, 0.1 mL of 2% sodium fluorescein (Akorn, Lake Forest, Ill.) was administered intraperitoneally, and subsequent serial photographs from early phase (0-60 seconds after injection) and late phase (6 minutes after injection) were captured using Micron III imaging system (Phoenix Research Labs, Pleasanton, Calif., USA). Light source intensity and gain was standardized and maintained for all experiments.

Nanoemulsion Manufacturing Process

Briefly, soy lecithin was extracted in sterile conditions from commercially available capsules and mixed with isopropyl myristate (Millipore Sigma, Merck KGaA, Darmstadt, Germany) in a 1:1 proportion as surfactant and organic phase, respectively. Then, CBFβ-Runx1 Inhibitor II, Ro5-3335 (Millipore Sigma, Merck KGaA, Darmstadt, Germany) was added to the mixture, and then diluted in PBS to reach a final concentration of 7.92 mM. Subsequently, the mixture was homogenized at 4000 rpm for 6 min with a PT10-35 GT Kinematica Polytron™ homogenizer (Kinematica AG, Switzerland) and subjected to sonication with a Qsonica XL-2000 sonicator (Qsonica LLC, Newtown, Conn.) at 15 kW of power for 10 min in ice to avoid excessive heating of the product. For the vehicle production, the same protocol was followed without adding Ro5-3335 to the mixture.

Study Groups and Treatment Application

Three study groups were created: Baseline, eNano Vehicle and eNanoRo5. For the baseline group, no treatment was performed as an internal control for the vehicle treatment. On the other hand, for the interventional groups (eNano Vehicle and eNanoRo5) 20 µl of nanoemulsion were topically instilled over ocular surface with a pipette in a QID regimen during 7 days. Mice were manually restrained for 60 seconds after topical application of the treatment to avoid washing reaction from the animals.

Quantification of CNV Size

To measure CNV complex surface area, choroidal flatmounts were performed. Eyes were enucleated and fixed in 4% paraformaldehyde for 2 hours at 4° C. Briefly, cornea, lens and retina were removed, and eight petals are created by cutting the remaining eyecup. Choroidal flatmounts were blocked with 1% BSA, 0.1% Triton x-100, and 3% donkey serum in PBlec buffer overnight at 4° C., incubated with Isolectin IB4 (Alexa Fluor 488 Conjugate, Life Technologies, 1:100) overnight at 4° C. and then mounted in 50% glycerol. Samples were imaged with an EVOS FL Auto imaging system (Life technologies, Carlsbad, Calif.) at 20× magnification, and randomized and blinded before analysis with ImageJ (ref). CNV lesion inclusion and exclusion criteria were established before quantification as previously published. (Gong, Y., et al., Optimization of an Image-Guided Laser-Induced Choroidal Neovascularization Model in Mice. PloS one 10, e0132643; 2015, and Poor, S. H. et al., Reliability of the mouse model of choroidal neovascularization induced by laser photocoagulation. Investigative Ophthalmology & Visual Science 55, 6525-6534; 2014) Image J version 2.0.0 (developed by Wayne Rasband, National Institutes of Health, Bethesda, Md.; available at http://rsb.info.nih.gov/ij/index.html) with Versatile Wand tool plug in (Versatile Wand Tool. Available at: https://imagej.nih.gov/ij/plugins/versatile-wand-tool/index.html).

Figure 11:
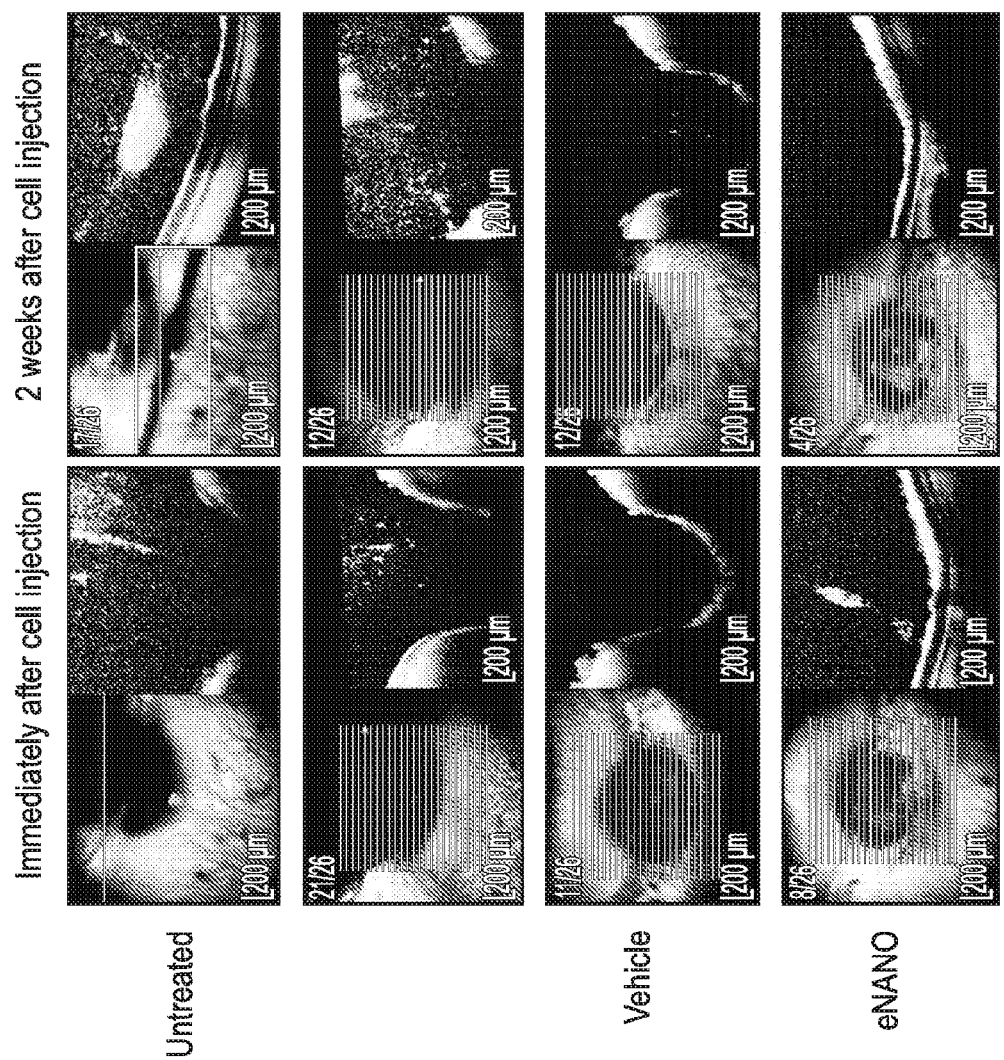
FIG. 11 is a series of images that depict cell proliferation response to different treatment modalities in a model of PVR in rabbits. Funduscopic (left) and Optical Coherence Tomography (OCT) (right) representative images after C-PVR cell injection in rabbits is shown. In the untreated group, cells were easily identified over the optic nerve area after cell injection, two weeks after the injection, cell proliferation and formation of intravitreal membranes and floaters is noted. Similarly, cell proliferation is increased after 2 weeks of follow up in the vehicle treated group. After 2 weeks of follow-up, cells were no longer identified over optic nerve head area in the eNANO (eNanoRo5) treated group.

Cell Proliferation Response to Different Treatment Modalities in a Model of PVR in Rabbits The cell proliferation response to different treatment modalities was studied in a model of PVR in rabbits (FIG. 11). Funduscopic (FIG. 11, left panel) and Optical Coherence Tomography (OCT) (FIG. 11, right panel) depict representative images after C-PVR cell injection in rabbits. In the untreated group, cells were easily identified over the optic nerve area after cell injection. Two weeks after the injection, cell proliferation and formation of intravitreal membranes and floaters were observed. Similarly, cell proliferation was increased after 2 weeks of follow up in the vehicle treated group. Interestingly, after 2 weeks of follow-up, cells were no longer identified over optic nerve head area in the eNanoRo5 treated group. These data indicated that topical application of eNanoRo5 can inhibit the proliferation of C-PVR cells in vivo.

Methods

Induction of Experimental PVR

Male and female New Zealand White rabbits (2,3 kg of weight) were purchased from Charles River (Charles River Laboratories, Inc., Wilmington, Mass.). Before every procedure, animals were anesthetized by intramuscular injection of Ketamine (30-50 mg/Kg) (KetaVed®, Vedco Inc., St. Joseph, Mo., USA), Xylazine (5-10 mg/kg) (Anased®, Akorn Animal Health, Lake Forest, Ill.) and Acepromazine (0.75 mg/Kg) (Phoenix Pharmaceuticals Inc., Burlingame, Calif.). Also, a subcutaneous injection of Buprenorphine (0.05-0.1 mg/kg) (Buprenex®, Reckitt Benckiser Inc., Richmond, Va.) was administered. Pupils were dilated with topical application of 1% Tropicamide drops (Bausch and Lomb Inc., Tampa, Fla.) and anesthetic drops of 0.5% Proparacaine (Bausch and Lomb Inc., Tampa, Fla.) were also applied. The right eye of each animal was used to develop the model, and left eyes were used as control. Gas vitrectomy was induced by intravitreal injection of 0.15 mL of perfluoropropane ($C_3F_8$) (Alcon, Forth Worth, Tex.) 4 mm behind the limbus. Three days after gas vitrectomy, intraocular pressure (IOP) was reduced by gas withdrawal, and 0.2 mL of aqueous humor extraction. Subsequently, 0.2 mL of balanced salt solution (BSS) containing approximately $1 \times 10^6$ C-PVR cells were injected intravitreally. These cells were obtained and processed following previously published method (Amarnani, D., et al., Effect of Methotrexate on an In Vitro Patient-Derived Model of Proliferative Vitreoretinopathy. Investigative Ophthalmology & Visual Science 58, 3940-3949; 2017). Intraocular pressure (TOP) monitoring with Tonopen (Reichert Technologies, N.Y. USA), and topical postoperative treatment with 0.5% Timolol b.i.d. (Akorn, Lake Forest, Ill.), 0.3% Ofloxacin t.i.d. (Akorn, Lake Forest, Ill.) and Triple antibiotic ointment (Akorn, Lake Forest, Ill.) q.h.s., were performed for 3 days. Under deep anesthesia, animals were euthanized and the eyes were collected after 28 days of follow-up, by injection of pentobarbital (120 mg/Kg) (Fatal Plus®, Vortech, Dearborn, Mich., USA). The experiments were performed in accordance with MEE Institutional Animal Care and Use Committee regulation, and with guidelines for the Use of Animals in Ophthalmic and Vision Research of the Association for Research in Vision and Ophthalmology.

Experimental Groups

A total of 21 rabbits were included in the study divided in three groups: Untreated (n=9), vehicle (n=6) and eNanoRo5 treatment (n=6). Topical treatment with 100 µl of eNanoRo5 emulsion or eNano Vehicle was initiated immediately after cell injection at a concentration of 7.92 mM three times a day during 28 days. One animal from eNanoRo5 group was excluded from the study because of a vitreous hemorrhage.

Nanoemulsion (eNanoRo5) Manufacturing Process

Briefly, soy lecithin was extracted in sterile conditions from commercially available capsules and mixed with isopropyl myristate (Millipore Sigma, Merck KGaA, Darmstadt, Germany) in a 1:1 proportion as surfactant and organic phase, respectively. Then, Ro5-3335 (Millipore Sigma, Merck KGaA, Darmstadt, Germany) was added to the mixture, and PBS was added to reach the final concentration of 7.92 mM. Subsequently, the mixture was homogenized at 4000 rpm for 6 min with a PT10-35 GT Kinematica Polytron™ homogenizer (Kinematica AG, Switzerland) and subjected to sonication with a Qsonica XL-2000 sonicator (Qsonica LLC, Newtown, Conn.) at 15 kW of power for 10 min in ice to avoid excessive heating of the product. For the vehicle production (eNano Vehicle), the same protocol was followed without adding Ro5-3335 to the mixture.

Clinical Evaluation

Rabbits were examined by indirect ophthalmoscopy after cell injection 1 week, 2 weeks and 4 weeks. For fundus and optical coherence tomography (OCT) imaging, a spectral-domain OCT Spectralis (Heidelberg Engineering, Heidelberg, Germany) was used immediately after cell injection, at 2 weeks and 4 weeks of follow-up. To grade PVR severity, a PVR Score was designed by combination of both assessment methods. The score was determined by the worst phenotype identified in the exploration.

| PVR Score | | | |
|---|---|---|---|
| Score | Clinical (Ophthalmoscopy + Fundus images) | Score | OCT (Optical Coherence Tomography) |
| 0 | No cells visible | 0 | No cells visible |
| 1 | Cells present in fundus images/floaters | 1 | Cells present (Low cellularity, floaters) |
| 2 | Cells organized as membranes (intravitreal membranes) | 2 | Cells present (Great cellularity, intravitreal membranes) |
| 3 | Vitreous strands attached to the retina (no traction) | 3 | Vitreous stands, intravitreal membranes attached to the retina without traction |
| 4 | Focal traction/Vascular changes | 4 | Intravitreal membranes attached to the retina with focal traction |
| 5 | Broad traction/Vascular changes/Hemorrhages | 5 | Intravitreal membranes attached to the retina with broad traction |
| 6 | Focal RD | 6 | Focal RD |
| 7 | Extensive RD/Holes/Tears | 7 | Extensive RD/Holes/Tears |
| 1 | Presence of retrolental proliferation | | |

Additionally, to analyze ocular safety and tolerability of the emulsion in the anterior segment, a semi-quantitative preclinical ocular toxicology scoring (SPOTS) system, based on McDonald-Shadduck and Hackett-McDonald scales, was used. (Eaton, et al. *Journal of Ocular Pharmacology and Therapeutics: The Official Journal of the Association for Ocular Pharmacology and Therapeutics* 33, 718-734 (2017)).

Figure 15:
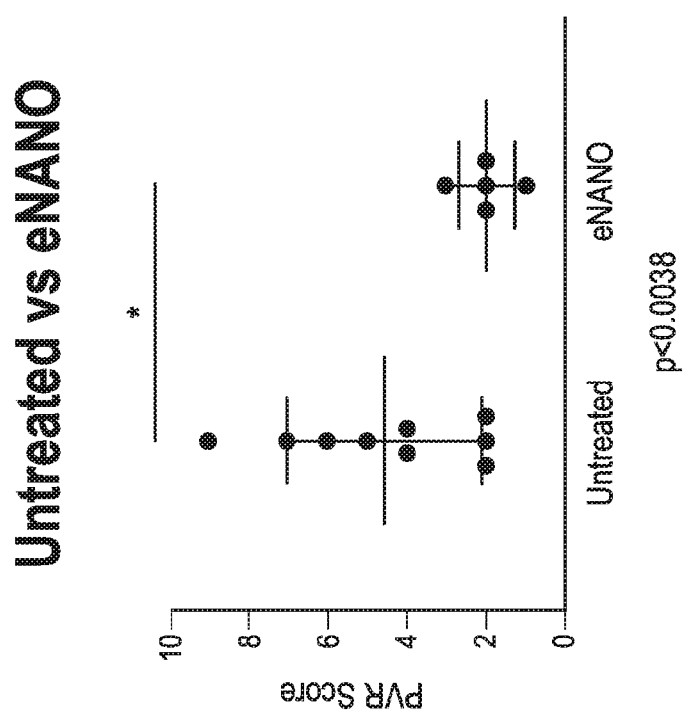
FIG. 15 is a graph depicting a study groups comparison after 2 weeks of follow-up. For 2 groups comparisons, a t-test, non-parametric with Mann-Whitney analysis was used. ANOVA was used for the 3 group comparison.

Example 8: In Vivo Efficacy of Emulsion on a Rabbit Model of Proliferative Vitreoretinopathy The in vivo efficacy of the emulsion on a rabbit model of proliferative vitreoretinopathy was studied (FIG. 15). For example, FIG. 15 depicts a graph of a study group comparison after 2 weeks of follow-up. A significant decrease in the PVR score in rabbits treated with topical eNanoRo5 was observed as compared to eNano Vehicle control. These data indicated that eNanoRo5 can inhibit PVR in vivo. Also, an anterior segment toxicity was evaluated, and the results are shown in Table 1 below.

TABLE 1

Anterior segment toxicity score after 2 weeks of follow-up.

| | Vehicle | | | | | | eNanoRo5 | | | | |
|---|---|---|---|---|---|---|---|---|---|---|---|
| | A19 | A20 | A21 | A25 | A27 | A29 | A22 | A24 | A26 | A28 | A30 |
| Conjunctival hyperemia | 0 | 0 | 0 | 0 | 0 | 0 | 0 | 0 | 0 | 0 | 1 |
| Conjunctival swelling | 0 | 0 | 0 | 0 | 0 | 0 | 0 | 0 | 0 | 0 | 0 |
| Conjunctival discharge | 0 | 0 | 0 | 0 | 0 | 0 | 0 | 0 | 0 | 0 | 0 |
| Corneal opacity Severity | 0 | 0 | 0 | 0 | 0 | 0 | 0 | 0 | 0 | 0 | 0 |
| Area | 0 | 0 | 0 | 0 | 0 | 0 | 0 | 0 | 0 | 0 | 0 |
| Corneal vascularization | 0 | 0 | 0 | 0 | 0 | 0 | 0 | 0 | 0 | 0 | 0 |
| Iris involvement | 0 | 0 | 0 | 0 | 0 | 0 | 0 | 0 | 0 | 0 | 0 |
| Lens | 0 | 0 | 0 | 0 | 0 | 0 | 0 | 0 | 0 | 0 | 0 |

Anterior segment toxicity score results were obtained following the Semi-quantitative Preclinical Ocular Toxicology Scoring System (SPOTS) guidelines[1] Treatments were topically applied t.i.d during 14 days.

[1] Eaton, J. S. et al. The SPOTS System: An Ocular Scoring System Optimized for Use in Modern Preclinical Drug Development and Toxicology. Journal of Ocular Pharmacology and Therapeutics: The Official Journal of the Association for Ocular Pharmacology and Therapeutics 33, 718-734 (2017)

As evidenced by Table 1 above, there was no evidence of anterior segment toxicity in the eNano Vehicle and the eNanoRo5 groups.

Example 9: Simulated Data (Solubility, Stability, and Effective Ocular Concentration) Using 7-fluoro-1,3-dihydro-5-(1H-pyrrol-2-yl)-2H-1,4-benzodiazepin-2-one and Ro5-3335

Structure and Modification of Ro5-3335

Figure 16:
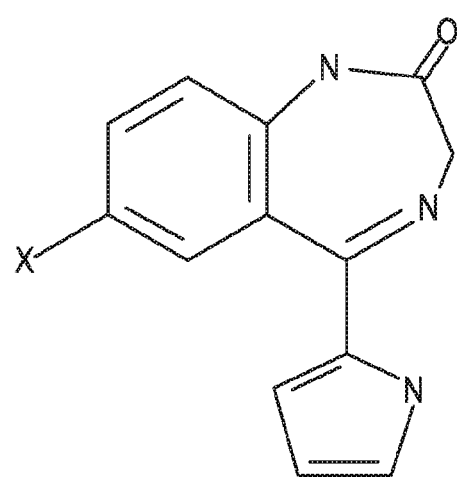
FIG. 16 depicts an image of a structure of an exemplary Ro5-3335 molecule. Ro5-3335 has issues of low solubility and photosensitivity which are likely related to the presence of chlorine (Cl) atom in the X position. The chlorine atom was changed t to a fluorine (F) atom, which is more electronegative. The chemical name of the new molecule is 7-fluoro-1,3-dihydro-5-(1H-pyrrol-2-yl)-2H-1,4-benzodiazepin-2-one. Using modeling software, the solubility was increased by a factor of two. Ro5-3335 solubility: 0.0113 mg/mL, and 7-fluoro-1,3-dihydro-5-(1H-pyrrol-2-yl)-2H-1, 4-benzodiazepin-2-one solubility: 0.0215 mg/mL

Ro5-3335 has issues of low solubility and photosensitivity which are likely related to the presence of the chlorine (Cl) atom. To address these issues, the chlorine atom was changed to a fluorine (F) atom, which is more electronegative (FIG. 16). Specifically, for Ro5-3335 a chlorine is placed at position X, whereas for the proposed molecule Ro5-3335 was modified with a fluorine placed at position X. The chemical name of the new molecule is 7-fluoro-1,3-dihydro-5-(1H-pyrrol-2-yl)-2H-1,4-benzodiazepin-2-one. Calculations indicated that this change increases the solubility by a factor of two. The solubility for Ro5-3335 is 0.0113 mg/mL, and for 7-fluoro-1,3-dihydro-5-(1H-pyrrol-2-yl)-2H-1,4-benzodiazepin-2-one, the solubility is 0.0215 mg/mL.

Simulated Solubility Data

Figure 17A:
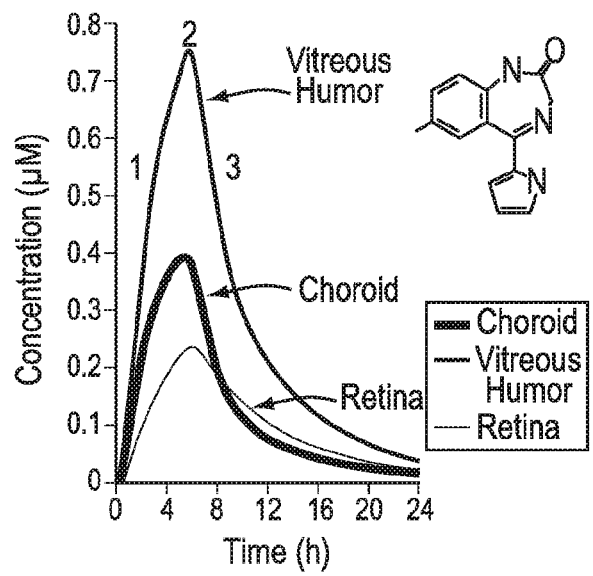
FIG. 17A depicts an image of a graph of a concentration profile in different eye compartments from a 7.92 mM topical eye-drop suspension of Ro5-3335 (7-chloro-1,3-dihydro-5-(1h-pyrrol-2y-yl)-2H-1,4-benzodiazepin-2-one), particle size 10 nm in rabbits, and administration of 1 drop (25 µL) for 24 h. The graph represents the drug distribution in the choroid, vitreous humor, and retina. Three main stages are shown in the graph and correspond to absorption (1), distribution peak height (2) and elimination of the drug.
Figure 17B:
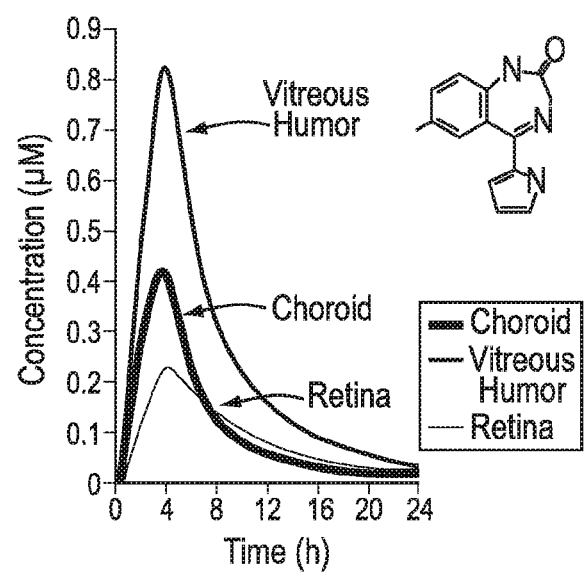
FIG. 17B depicts an image of a graph of a concentration profile in different eye compartments from a 7.92 mM topical eye-drop suspension of 7-fluoro-1,3-dihydro-5-(1h-pyrrol-2y-yl)-2H-1,4-benzodiazepin-2-one, particle size 10 nm in rabbits, and administration of 1 drop (25 µL) for 24 h. The graph represents the drug distribution in the choroid, vitreous humor, and retina. Three main stages are shown in the graph and correspond to absorption (1), distribution peak height (2) and elimination of the drug.

The concentration profile in different eye compartments were evaluated. A 7.92 mM topical eye-drop suspension of Ro5-3335 ((7-chloro-1,3-dihydro-5-(1h-pyrrol-2y-yl)-2H-1,4-benzodiazepin-2-one)) (FIG. 17A)) and 7-fluoro-1,3-dihydro-5-(1h-pyrrol-2y-yl)-2H-1,4-benzodiazepin-2-one (FIG. 17B), at a particle size of 10 nm in rabbits, and administration of 1 drop (25 µL) for 24h was evaluated. FIG. 17A and FIG. 17B represent the drug distribution in the choroid, vitreous humor and retina. Three main stages are shown in the graph and corresponds to absorption (1), distribution peak height (2) and elimination of the drug (3). 7-fluoro-1,3-dihydro-5-(1h-pyrrol-2y-yl)-2H-1,4-benzodiazepin-2-one had a higher distribution peak compared to Ro5-3335. However, Ro5-3335 (FIG. 17A) showed a retarded elimination in contrast to the modified molecule, due to physicochemical properties. The simulations were conducted using a commercially available software called GastroPlus™ (from SimulationsPlus). The ocular model used was the compartmental pharmacokinetics model, which considered multiple compartments of the eye with transport of drugs between each tissue modeled by a concentration gradient. Drug-diffusion rates depended on physiological and physicochemical properties of each compartment. In addition, this model considered mechanisms critical to topical administration such as nasolacrimal drainage.

Simulated Stability Data

Figure 18A:
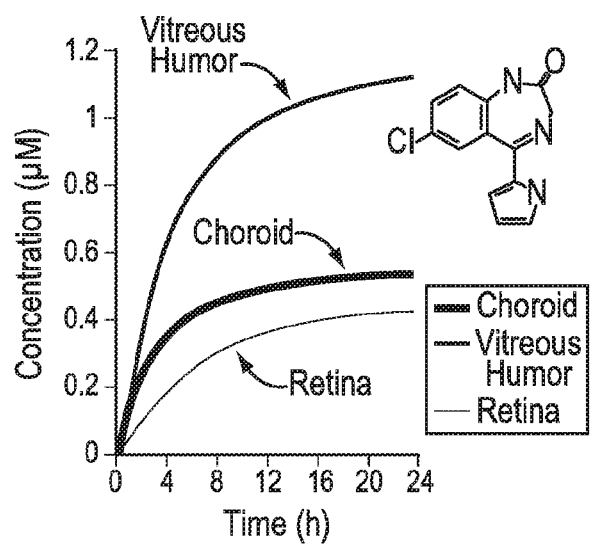
FIG. 18A depicts an image of a graph of a concentration profile in different eye compartments from a 7.92 mM topical eye-drop suspension of Ro5-3335, particle size 10 nm in rabbits, and administration of 2 (50 µL) drops for 24 hours, every four hours. Multiple administration allowed higher concentration of the modified molecule in each compartment.
Figure 18B:
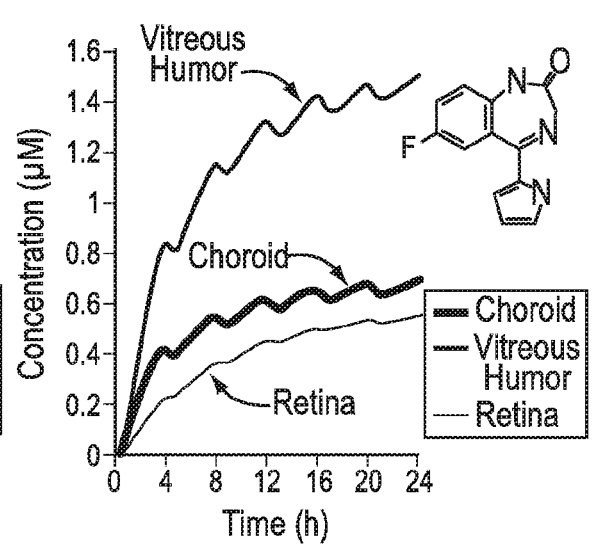
FIG. 18B depicts an image of a graph of a concentration profile in different eye compartments from a 7.92 nM topical eye-drop suspension of 7-fluoro-1,3-dihydro-5-(1h-pyrrol-2y-yl)-2H-1,4-benzodiazepin-2-one, particle size 10 nm in rabbits, and administration of 2 (50 µL) drops for 24h every 4h. Multiple administration allows higher concentration of the modified molecule in each compartment. However, due to its oscillate response, the drug absorption showed reversibility. This data showed that 7-fluoro-1,3-dihydro-5-(1h-pyrrol-2y-yl)-2H-1,4-benzodiazepin-2-one achieved higher effective concentrations in the vitreous, which is a highly desirable feature for efficacy.

Furthermore, the concentration profile in different eye compartments from a 7.92 mM topical eye-drop suspension of Ro 5-3335 (FIG. 18A) and 7-fluoro-1,3-dihydro-5-(1h-pyrrol-2y-yl)-2H-1,4-benzodiazepin-2-one (FIG. 18B), at a particle size 10 nm in rabbits, and administration of 2 (50 µL) drops for 24 h every 4 h was evaluated. Multiple administration allowed higher concentration of the modified molecule (FIG. 18B) in each compartment. However, due to its oscillate response, the drug absorption showed reversibility. These data showed that 7-fluoro-1,3-dihydro-5-(1h-pyrrol-2y-yl)-2H-1,4-benzodiazepin-2-one (FIG. 18B) was predicted to achieve higher effective concentrations in the vitreous, which is a highly desirable feature for efficacy.

Simulated Effective Ocular Concentration Data

The concentration of therapeutic agents in plasma from a 7.92 mM topical eye-drop suspension of Ro5-3335 (FIG. 19A) and 7-fluoro-1,3-dihydro-5-(1h-pyrrol-2y-yl)-2H-1,4-benzodiazepin-2-one (FIG. 19B), at a particle size 10 nm in rabbits, and administration of 2 (50 µL) drops for 24 h every 4 h, was evaluated.

Figure 19A:
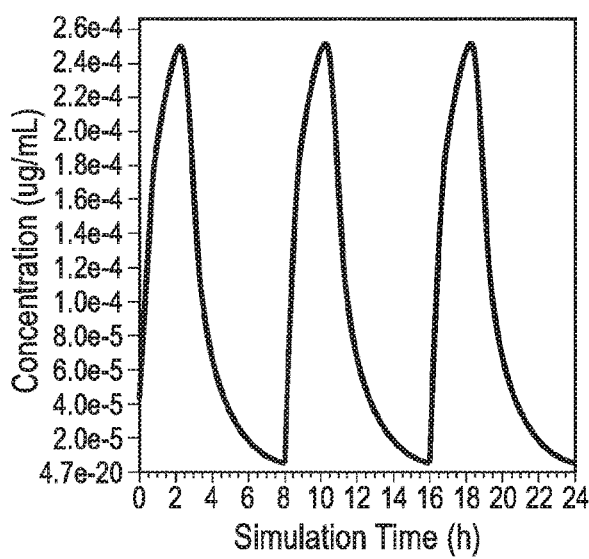
FIG. 19A depicts an image of a graph of the concentration of therapeutic agents in plasma from a 7.92 mM topical eye-drop suspension of Ro 5-3335, particle size 10 nm in rabbits, and administration of 2 (50 µL) drops for 24 h every 4 h. The graph showed the plasma concentration of Ro5-3335, and showed that the elimination stage of Ro5-3335 was achieved in a shorter time frame, and was eliminated after 8 hours but overall reached much higher levels compared to the modified molecule (FIG. 19B).
Figure 19B:
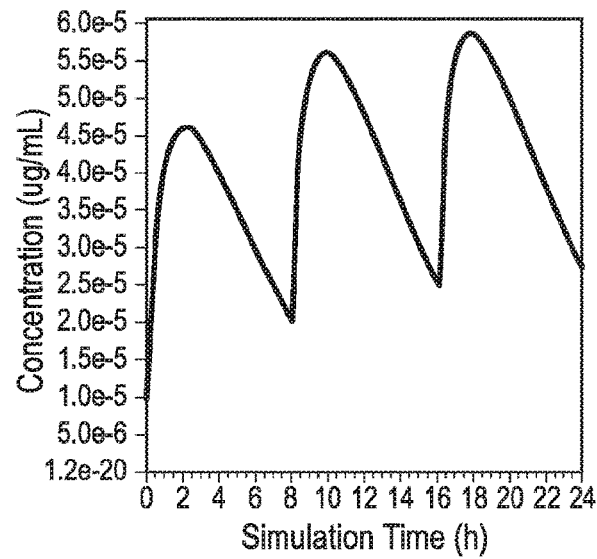
FIG. 19B depicts an image of a graph of a concentration of therapeutic agents in plasma from a 7.92 mM topical eye-drop suspension of 7-fluoro-1,3-dihydro-5-(1h-pyrrol-2y-yl)-2H-1,4-benzodiazepin-2-one, particle size 10 nm in rabbits, and administration of 2 (50 µL) drops for 24 h every 4 h. The graph showed the plasma concentration of 7-fluoro-1,3-dihydro-5-(1h-pyrrol-2y-yl)-2H-1,4-benzodiazepin-2-one, and showed that the molecule was expected to be found at much lower concentrations in the blood, which was expected to limit toxicity.

Toxicological and pharmacological actions of medicines are related to their concentration in plasma, controlled by ADME (Absorption, Distribution, Metabolism, and Excretion). The pharmacokinetics influenced the amount and frequency of each dose and the route of administration in order to diminish collateral effects and improve effective action. Absorption from targeted drug delivery allows entry of the molecule indirectly into plasma. Once the therapeutic agent is absorbed, it may reversibly leave the bloodstream and is distributed. Later, the medicine is metabolized, which lead to medicine inactivation and excretion. FIGS. 19A and 19B showed the plasma concentration of Ro5-3335 (FIG. 19A) and 7-fluoro-1,3-dihydro-5-(1h-pyrrol-2y-yl)-2H-1,4-benzodiazepin-2-one (FIG. 19B). The elimination stage of Ro5-3335 (FIG. 19A) was achieved in a shorter time frame, and was eliminated after 8 hours, but overall reached much higher levels compared to the modified molecule (7-fluoro-1,3-dihydro-5-(1h-pyrrol-2y-yl)-2H-1,4-benzodiazepin-2-one) (FIG. 19B). On the contrary, the modified molecule was expected to be found at much lower concentrations in the blood, which is expected to limit toxicity (FIG. 19B).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:
1. A method of treating an ocular disorder or disease, comprising topically administering to an ocular tissue of a subject a composition in the form of a nano-emulsion comprising:
   (i) from about 1 to about 3% (v/v) of isopropyl myristate;
   (ii) lecithin;
   (iii) phosphate buffered saline; and

(iii) from about 0.01 mM to about 10 mM of a core binding factor β (CBFβ)-Runt Related Transcription Factor 1 (RUNX1) inhibitor dispersed within the isopropyl myristate, wherein the average particle size of the emulsion is about 200 nm or less, wherein the ocular disorder or disease is proliferative vitreoretinopathy.

2. The method of claim 1, wherein the nano-emulsion comprises from about 3 mM to about 10 mM of the RUNX1 inhibitor.

3. The method of claim 1, wherein the RUNX1 inhibitor comprises Ro5-3335.

4. The method of claim 1, wherein the RUNX1 inhibitor comprises 7-fluoro-1,3-dihydro-5-(1h-pyrrol-2y-yl)-2H-1,4-benzodiazepin-2-one.

5. The method of claim 2, wherein the RUNX1 inhibitor comprises Ro5-3335.

6. The method of claim 2, wherein the RUNX1 inhibitor comprises 7-fluoro-1,3-dihydro-5-(1h-pyrrol-2y-yl)-2H-1,4-benzodiazepin-2-one.

* * * * *

UNITED STATES PATENT AND TRADEMARK OFFICE
CERTIFICATE OF CORRECTION

PATENT NO. : 11,583,497 B2
APPLICATION NO. : 16/763932
DATED : February 21, 2023
INVENTOR(S) : Leo A. Kim and Joseph F. Arboleda-Velasquez Page 1 of 1

It is certified that error appears in the above-identified patent and that said Letters Patent is hereby corrected as shown below:

In the Specification

Column 1, Lines 14, insert -- STATEMENT OF FEDERALLY SPONSORED RESEARCH
This invention was made with government support under Grant No. EY021624 awarded by the National Institutes of Health. The government has certain rights in the invention. --

Signed and Sealed this
Twenty-third Day of May, 2023

Katherine Kelly Vidal
*Director of the United States Patent and Trademark Office*